United States Patent
Liu et al.

(10) Patent No.: US 11,091,742 B2
(45) Date of Patent: Aug. 17, 2021

(54) DIRECTED EVOLUTION OF CYP52A12 GENE AND ITS USE IN DICARBOXYLIC ACID PRODUCTION

(71) Applicants: CATHAY BIOTECH INC., Shanghai (CN); CIBT AMERICA INC., Newark, DE (US)

(72) Inventors: Wenbo Liu, Shanghai (CN); Min Xu, Shanghai (CN); Howard Chou, Shanghai (CN); Xiucai Liu, Shanghai (CN)

(73) Assignees: CATHAY BIOTECH INC., Shanghai (CN); CIBT AMERICA INC., Newark, DE (US)

( * ) Notice: Subject to any disclaimer, the term of this patent is extended or adjusted under 35 U.S.C. 154(b) by 55 days.

(21) Appl. No.: 16/229,084

(22) Filed: Dec. 21, 2018

(65) Prior Publication Data

US 2019/0309270 A1   Oct. 10, 2019
US 2021/0180032 A9   Jun. 17, 2021

(30) Foreign Application Priority Data

Apr. 4, 2018 (CN) .......................... 201810299532.8
Nov. 28, 2018 (CN) .......................... 201811433497.0

(51) Int. Cl.
*C12N 9/02* (2006.01)
*C12N 15/00* (2006.01)
(Continued)

(52) U.S. Cl.
CPC ............ *C12N 9/0071* (2013.01); *C12N 15/52* (2013.01); *C12N 9/001* (2013.01); *C12P 7/6409* (2013.01); *C12Y 114/14* (2013.01)

(58) Field of Classification Search
CPC .................................................. C12N 9/0071
See application file for complete search history.

(56) References Cited

U.S. PATENT DOCUMENTS 10,202,620 B2 * 2/2019 Coelho ................. C12P 7/6418
2016/0108436 A1 * 4/2016 Coelho ................... C07C 29/32
435/157

FOREIGN PATENT DOCUMENTS

CN     103243032 A     8/2013
JP     2011101643 A    5/2011
(Continued)

OTHER PUBLICATIONS

Studer (Residue mutations and their impact on protein structure and function: detecting beneficial and pathogenic changes. Biochem. J. (2013) 449, 581-594.*
Craft. Q874J5_CANTR. UnitProtKB Database. 2017.*
European Search Report issued in Application No. 18215532.5 dated Jul. 30, 2019, 14 pages.
(Continued)

*Primary Examiner* — Yong D Pak
(74) *Attorney, Agent, or Firm* — Rothwell, Figg, Ernst & Manbeck, P.C.

(57) ABSTRACT

The invention relates to the directed evolution of CYP52A12 gene and the use thereof for the production of a dicarboxylic acid. In particular, it relates to a method of preparing a long chain dicarboxylic acid producing strain by using directed evolution and homologous recombination, a strain obtained by the method that is capable of producing a long chain dicarboxylic acid under an acidic condition and the use thereof. In particular, the invention relates to a method of preparing a long chain dicarboxylic acid producing strain by directed evolution of CYP52A12 gene and homologous recombination, a strain obtained by the method that is capable of producing a long chain dicarboxylic acid under an acidic condition and the use thereof. By directed evolution of CYP52A12 gene, one strain which has a base mutation at the promoter region of said gene and is capable (Continued)

of producing a long chain dicarboxylic acid under an acidic condition in a shortened fermentation time is screened out in the invention.

2 Claims, 3 Drawing Sheets

Specification includes a Sequence Listing.

(51) Int. Cl.
*C12N 15/52* (2006.01)
*C12P 7/64* (2006.01)

(56) References Cited

FOREIGN PATENT DOCUMENTS

| WO | 2014100461 A2 | 6/2014 |
|----|---------------|--------|
| WO | 2014100504 A2 | 6/2014 |

OTHER PUBLICATIONS

Communication pursuant to Article 94(3) EPC dated Jul. 7, 2020 issued in European Patent Application No. 18215532.5, (4 pages).
The partial European Search Report issued in Application No. 18215532.5 dated Apr. 24, 2019, 17 pages.
Database UniProt [Online], "SubName: Full=Cytochrome P450 52A6 {ECO:0000313: EMBL: EER33907.1};", XP002790349, retrieved from EBI accession No. UNIPROT: C5M8K3, Jul. 28, 2009, 1 page.
Database JPO Proteins [Online], "JP 2011101643-A/52: Candida tropicalis cells and use thereof.", XP002790350, retrieved from EBI accession No. JPOP: DJ762966, Aug. 24, 2012, 1 page.
Database EMBL [Online], "JP 2011101643-A/18: Candida tropicalis cells and use thereof.", XP002790351, retrieved from EBI accession No. EM_PAT: HV339614, Aug. 30, 2011, 1 page.
Database UniProt [Online], "RecName: Full=Cytochrome P450 52A3-B; Short=CYP52A3-B; EC=1.14.14-; AltName: Full=Alkane-inducible P450-ALK1-B;AltName: Full=CYPLIIA3;", XP002790352, retrieved from EBI accession No. UNIPROT: P24458, Mar. 1, 1992, 1 page.

* cited by examiner

```
CCTCC2011192    ATGGCCACACAAGAAATCATCGATTCTGTACTTCCGTACTTGACCAAATGGTACACTGTG
CYP52A12_540    ATGGCCACACAAGAAATCATCGATTCTGTACTTCCGTACTTGACCAAATGGTACACTGTG
                ************************************************************

CCTCC2011192    ATTACTGCAGCAGTATTAGTCTTCCTTATCTCCACAAACATCAAGAACTACGTCAAGGCA
CYP52A12_540    ATTACTGCAGCAGTATTAGTCTTCCTTATCTCCACAAACATCAAGAACTACGTCAAGGCA
                ************************************************************

CCTCC2011192    AAGAAATTGAAATGTGTCGATCCACCATACTTGAAGGATGCCGGTCTCACTGGTATTCTG
CYP52A12_540    AAGAAATTGAAATGTGTCGATCCACCATACTTGAAGGATGCCGGTCTCACTGGTATTCTG
                ************************************************************

CCTCC2011192    TCTTTGATCGCCGCCATCAAGGCCAAGAACGACGGTAGATTGGCTAACTTTGCCGATGAA
CYP52A12_540    TCTTTGATCGCCGCCATCAAGGCCAAGAACGACGGTAGATTGGCTGACTTTGCCGATGAA
                ********************************************* **************

CCTCC2011192    GTTTTCGACGAGTACCCAAACCACACCTTCTACTTGTCTGTTGCCGGTGCTTTGAAGATT
CYP52A12_540    GTTTTCGACGAGTACCCAAACCACACCTTCTACTTGTCTGTTGCCGGTGCTTTGAAGATT
                ************************************************************

CCTCC2011192    GTCATGACTGTTGACCCAGAAAACATCAAGGCTGTCTTGGCCACCCAATTCACTGACTTC
CYP52A12_540    GTCATGACTGTTGACCCAGAAAACATCAAGGCTGTCTTGGCCACCCAATTCACTGACTTC
                ************************************************************

CCTCC2011192    TCCTTGGGTACCAGACACGCCCACTTTGCTCCTTTGTTGGGTGACGGTATCTTCACCTTG
CYP52A12_540    TCCTTGGGTACCAGACACGCCCACTTTGCTCCTTTGTTGGGTGACGGTATCTTCACCTTG
                ************************************************************

CCTCC2011192    GACGGAGAAGGTTGGAAGCACTCCAGAGCTATGTTGAGACCACAGTTTGCTAGAGACCAG
CYP52A12_540    GACGGAGAAGGTTGGAAGCACTCCAGAGCTATGTTGAGACCACAGTTTGCTAGAGACCAG
                ************************************************************

CCTCC2011192    ATTGGACACGTTAAAGCCTTGGAACCACACATCCAAATCATGGCTAAGCAGATCAAGTTG
CYP52A12_540    ATTGGACACGTTAAAGCCTTGGAACCACACATCCAAATCATGGCTAAGCAGATCAAGTTG
                ************************************************************

CCTCC2011192    AACCAGGGAAAGACTTTCGATATCCAAGAATTGTTCTTTAGATTTACCGTCGACACCGCT
CYP52A12_540    AACCAGGGAAAGACTTTCGATATCCAAGAATTGTTCTTTAGATTTACCGTCGACACCGCT
                ************************************************************

CCTCC2011192    ACTGAGTTCTTGTTTGGTGAATCCGTTCACTCCTTGTACGATGAAAAATTGGGCATCCCA
CYP52A12_540    ACTGAGTTCTTGTTTGGTGAATCCGTTCACTCCTTGTACGATGAAAAATTGGGCATCCCA
                ************************************************************

CCTCC2011192    ACTCCAAACGAAATCCCAGGAAGAGAAAACTTTGCCGCTGCTTTCAACGTTTCCCAACAC
CYP52A12_540    ACTCCAAACGAAATCCCAGGAAGAGAAAACTTTGCCGCTGCTTTCAACGTTTCCCAACAC
                ************************************************************

CCTCC2011192    TACTTGGCCACCAGAAGTTACTCCCAGACTTTTTACTTTTTGACCAACCCTAAGGAATTC
CYP52A12_540    TACTTGGCCACCAGAAGTTACTCCCAGACTTTTTACTTTTTGACCAACCCTAAGGAATTC
                ************************************************************

CCTCC2011192    AGAGACTGTAACGCCAAGGTCCACCACTTGGCCAAGTACTTTGTCAACAAGGCCTTGAAC
CYP52A12_540    AGAGACTGTAACGCCAAGGTCCACCACTTGGCCAAGTACTTTGTCAACAAGGCCTTGAAC
                ************************************************************

CCTCC2011192    TTTACTCCTGAAGAACTCGAAGAGAAATCCAAGTCCGGTTACGTTTTCTTGTACGAATTG
CYP52A12_540    TTTACTCCTGAAGAACTCGAAGAGAAATCCAAGTCCGGTTACGTTTTCTTGTACGAATTG
                ************************************************************
```

Figure 2

```
CCTCC2011192    GTTAAGCAAACCAGAGATCCAAAGGTCTTGCAAGATCAATTGTTGAACATTATGGTTGCC
CYP52A12_540    GTTAAGCAAACCAGAGATCCAAAGGTCTTGCAAGATCAATTGTTGAACATTATGGTTGCA
                ************************************************************

CCTCC2011192    GGAAGAGACACCACTGCCGGTTTGTTGTCCTTTGCTTTGTTTGAATTGGCTAGACACCCA
CYP52A12_540    GGAAGAGACACCACTGCCGGTTTGTTGTCCTTTGCTTTGTTTGAATTGGCTAGACACCCA
                ************************************************************

CCTCC2011192    GAGATGTGGTCCAAGTTGAGAGAAGAAATCGAAGTTAACTTTGGTGTTGGTGAAGACTCC
CYP52A12_540    GAGATGTGGTCCAAGTTGAGAGAAGAAATCGAAGTTAACTTTGGTGTTGGTGAAGACTCC
                ************************************************************

CCTCC2011192    CGCGTTGAAGAAATTACCTTCGAAGCCTTGAAGAGATGTGAATACTTGAAGGCTATCCTT
CYP52A12_540    CGCGTTGAAGAAATTACCTTCGAAGCCTTGAAGAGATGTGAATACTTGAAGGCTATCCTT
                ************************************************************

CCTCC2011192    AACGAAACCTTGCGTATGTACCCATCTGTTCCTGTCAACTTTAGAACCGCCACCAGAGAC
CYP52A12_540    AACGAAACCTTGCGTATGTACCCATCTGTTCCTGTCAACTTTAGAACCGCCACCAGAGAC
                ************************************************************

CCTCC2011192    ACCACTTTGCCAAGAGGTGGTGGTGCTAACGGTACCGACCCAATCTACATTCCTAAAGGC
CYP52A12_540    ACCACTTTGCCAAGAGGTGGTGGTGCTAACGGTACCGACCCAATCTACATTCCTAAAGGC
                ************************************************************

CCTCC2011192    TCCACTGTTGCTTACGTTGTCTACAAGACCCACCGTTTGGAAGAATACTACGGTAAGGAC
CYP52A12_540    TCCACTGTTGCTTACGTTGTCTACAAGACCCACCGTTTGGAAGAATACTACGGTAAGGAC
                ************************************************************

CCTCC2011192    GCTAACGACTTCAGACCAGAAAGATGGTTTGAACCATCTACTAAGAAGTTGGGCTGGGCT
CYP52A12_540    GCTAACGACTTCAGACCAGAAAGATGGTTTGAACCATCTACTAAGAAGTTGGGCTGGGCT
                ************************************************************

CCTCC2011192    TATGTTCCATTCAACGGTGGTCCAAGAGTCTGCTTGGGTCAACAATTCGCCTTGACTGAA
CYP52A12_540    TATGTTCCATTCAACGGTGGTCCAAGAATCTGCTTGGGTCAACAATTCGCCTTGACTGAA
                ***************************  ******************************

CCTCC2011192    GCTTCTTATGTGATCACTAGATTGGCCCAGATGTTTGAAACTGTCTCATCTGATCCAGGT
CYP52A12_540    GCTTCTTATGTGATCACTAGATTGGCCCAGATGTTTGAAACTGTCTCATCTGATCCAGGT
                ************************************************************

CCTCC2011192    CTCGAATACCCTCCACCAAAGTGTATTCACTTGACCATGAGTCACAACGATGGTGTCTTT
CYP52A12_540    CTCGAATACCCTCCACCAAAGTGTATTCACTTGACCATGAGTCACAACGATGGTGTCTTT
                ************************************************************

CCTCC2011192    GTCAAGATGTAA
CYP52A12_540    GTCAAGATGTAA
                ************
```

Figure 2 (continued)

SEQUENCE LISTING

```
<160> NUMBER OF SEQ ID NOS: 22

<210> SEQ ID NO 1
<211> LENGTH: 20
<212> TYPE: DNA
<213> ORGANISM: Artificial Sequence
<220> FEATURE:
<223> OTHER INFORMATION: primer CYP52A12-F

<400> SEQUENCE: 1
caaaacagca ctccgcttgt                                                   20

<210> SEQ ID NO 2
<211> LENGTH: 20
<212> TYPE: DNA
<213> ORGANISM: Artificial Sequence
<220> FEATURE:
<223> OTHER INFORMATION: primer CYP52A12-R

<400> SEQUENCE: 2
ggatgacgtg tgtggcttga                                                   20

<210> SEQ ID NO 3
<211> LENGTH: 5873
<212> TYPE: DNA
<213> ORGANISM: Artificial Sequence
<220> FEATURE:
<223> OTHER INFORMATION: vector pCIB2

<400> SEQUENCE: 3
gcgcccaata cgcaaaccgc ctctccccgc gcgttggccg attcattaat gcagctggca      60
cgacaggttt cccgactgga aagcgggcag tgagcgcaac gcaattaatg tgagttagct     120
cactcattag gcacccagg  ctttacactt tatgcttccg gctcgtatgt tgtgtggaat     180
tgtgagcgga taacaatttc acacaggaaa cagctatgac catgattacg aattcggtct     240
agtatgattg tcaataatga tgggtcatcg tttcctgatt cgacgttccc tgtggtgtcg     300
ttaaatagcc tgtctgaaat ctcctccatg attgtgttgg tgtgtgttgt ttgactttcc     360
caattgctta cattttttc ttcaaggatt cgctccaaaa tagacagaaa ttatcgcgac     420
aagtcagacg aacgtcgcac gaggcgaacc aaattcttta gaagcatacg aaaactcact     480
```

```
ttatttccat tagaagtatt aaattaacaa atatataata tacaggatac aaagtaaaag        540
cacgcttaag caaccaaagc ggaagcggta gcggattcgt atttccagtt aggtggcaag        600
acagcgacgg ttctgtagta tctggccaat ctgtggattc tagattcaat caaaatcaat        660
ctgaacttgg agtccttgtc ctttctgttt cttttccaagt gctttctgac agagacagcc       720
ttcttgatca agtagtacaa gtcttctggg atttctggag ccaaaccgtt ggatttcaag        780
attctcaaga tcttgttacc agtgacaacc ttggcttggg aaacaccgtg agcatctctc        840
aagataacac caatttgaga tggagtcaaa cccttctgg cgtacttgat gacttgttca         900
acaacttcgt cagaagacaa cttgaaccaa gatggagcgt tcttgagta tggaagagcg         960 gaggaggaaa tacctttacc ctaaaataac aagagctaat gttagtaatt tgaaaaaaaa       1020
gacgttgagc acgcacaccc catccacccc acaggtgaaa cacatcaaac gtagcaagaa       1080
caatagttgg ccctcccgtc aagggggcag gtaattgtcc aagtacttta gaaaagtatg       1140
tttttaccca taagatgaac acacacaaac cagcaaaagt atcaccttct gcttttcttg       1200
gttgaggttc aaattatgtt tggcaataat gcagcgacaa tttcaagtac ctaaagcgta       1260
tatagtaaca attctaggtc tgtatagtcg accgtaggtg aatcgtttac tttaggcaag       1320
accttgtccc tgataaagcc aggttgtact ttctattcat tgagtgtcgt ggtggtggta       1380
gtggtggttg attgggctgt tgtggtagta gtagtggttg tgatttggaa catacagatg       1440
aatgcatacg acccatgatg actgatttgt ttctttattg agttgatggt aagaaagaga       1500
agaagaggag gtaaaaaggt ggtagagtga aaaattttt tctcttaaaa gtgagagaga       1560
gaaagagaaa aatttcactg cgaaacaaat ggttgggac acgactttt tcaggaattt        1620 ttactcgaag cgtatatgca ggaaagttgt tgttagggaa tatggagcca caagagagct       1680
gcgaattcga gctcggtacc cggggatcct ctagagtcga cctgcaggca tgcgaacccg       1740
aaaatggagc aatcttcccc ggggcctcca aataccaact cacccgagag agagaaagag       1800
acaccaccca ccacgagacg gagtatatcc accaaggtaa gtaactcagg gttaatgata       1860
caggtgtaca cagctccttc cctagccatt gagtgggtat cacatgacac tggtaggtta       1920
caaccacgtt tagtagttat tttgtgcaat tccatgggga tcaggaagtt tggtttggtg       1980
ggtgcgtcta ctgattcccc tttgtctctg aaaatctttt ccctagtgga cactttggc       2040 tgaatgatat aaattcacct tgattcccac cctcccttct ttctctctct ctctgttaca       2100
cccaattgaa ttttctttt tttttacctt tccctccttc tttatcatca aagataagta       2160
agtttatcaa ttgcctattc agaatgaaaa agcctgaact caccgcgacg tctgtcgaga       2220
agtttctcat cgaaaagttc gacagcgtct ccgacctcat gcagctctcg gagggcgaag       2280
aatctcgtgc tttcagcttc gatgtaggag ggcgtggata tgtcctccgg gtaaatagct       2340
gcgccgatgg tttctacaaa gatcgttatg tttatcggca ctttgcatcg gccgcgctcc       2400
cgattccgga agtgcttgac attggggaat tcagcgagag cctcacctat gcatctccc        2460 gccgtgcaca gggtgtcacg ttgcaagacc tcctgaaac cgaactcccc gctgttctcc       2520
agccggtcgc ggaggccatg gatgcgatcg ctgcggccga tcttagccag acgagcgggt       2580
tcggcccatt cggaccgcaa ggaatcggtc aatacactac atggcgtgat ttcatatgcg       2640
cgattgctga tccccatgtg tatcactggc aaactgtgat ggacgacacc gtcagtgcgt       2700
ccgtcgcgca ggctctcgat gagctcatgc tttgggccga ggactgcccc gaagtccggc       2760
acctcgtgca cgcggatttc ggctccaaca atgtcctcac ggacaatggc cgcataacag       2820
```

-continued

```
cggtcattga ctggagcgag gcgatgttcg gggattccca atacgaggtc gccaacatct    2880
tcttctggag gccgtggttg gcttgtatgg agcagcagac gcgctacttc gagcggaggc    2940
atccggagct tgcaggatcg ccgcggctcc gggcgtatat gctccgcatt ggtcttgacc    3000
aactctatca gagcttggtt gacggcaatt tcgatgatgc agcttgggcg cagggtcgat    3060
gcgacgcaat cgtccgatcc ggagccggga ctgtcgggcg tacacaaatc gcccgcagaa    3120
gcgcggccgt ctggaccgat ggctgtgtag aagtactcgc cgatagtgga aaccgacgcc    3180
ccagcactcg tccgagggca aggaatagt gtgctaccca cgcttactcc accagagcta    3240
ttaacatcag aaatatttat tctaataaat aggatgcaaa aaaaaaaccc cccttaataa    3300 aaaaaaaga acgatttttt tatctaatga agtctatgta tctaacaaat gtatgtatca    3360
atgtttattc cgttaaacaa aaatcagtct gtaaaaaagg ttctaaataa atattctgtc    3420
tagtgtacac attctcccaa aatagtgaaa tccagctgct agcgtgtaag cttggcactg    3480
gccgtcgttt tacaacgtcg tgactgggaa accctggcg ttacccaact taatcgcctt    3540
gcagcacatc cccctttcgc cagctggcgt aatagcgaag aggcccgcac cgatcgccct    3600
tcccaacagt tgcgcagcct gaatggcgaa tggcgcctga tgcggtattt tctccttacg    3660
catctgtgcg gtatttcaca ccgcatatgg tgcactctca gtacaatctg ctctgatgcc    3720
gcatagttaa gccagccccg acacccgcca cacccgctg acgcgccctg acgggcttgt    3780
ctgctcccgg catccgctta cagacaagct gtgaccgtct ccgggagctg catgtgtcag    3840
aggttttcac cgtcatcacc gaaacgcgcg agacgaaagg gcctcgtgat acgcctattt    3900
ttataggtta atgtcatgat aataatggtt tcttagacgt caggtggcac ttttcgggga    3960
aatgtgcgcg gaacccctat ttgtttattt ttctaaatac attcaaatat gtatccgctc    4020
atgagacaat aaccctgata aatgcttcaa taatattgaa aaaggaagag tatgagtatt    4080
caacatttcc gtgtcgccct tattcccttt tttgcggcat tttgccttcc tgtttttgct    4140
cacccagaaa cgctggtgaa agtaaaagat gctgaagatc agttgggtgc acgagtgggt    4200
tacatcgaac tggatctcaa cagcggtaag atccttgaga gttttcgccc cgaagaacgt    4260
tttccaatga tgagcacttt taaagttctg ctatgtggcg cggtattatc ccgtattgac    4320
gccgggcaag agcaactcgg tcgccgcata cactattctc agaatgactt ggttgagtac    4380
tcaccagtca cagaaaagca tcttacggat ggcatgacag taagagaatt atgcagtgct    4440
gccataacca tgagtgataa cactgcggcc aacttacttc tgacaacgat cggaggaccg    4500
aaggagctaa ccgcttttt gcacaacatg ggggatcatg taactcgcct tgatcgttgg    4560
gaaccggagc tgaatgaagc cataccaaac gacgagcgtg acaccacgat gcctgtagca    4620
atggcaacaa cgttgcgcaa actattaact ggcgaactac ttactctagc ttcccggcaa    4680
caattaatag actggatgga ggcggataaa gttgcaggac cacttctgcg ctcggccctt    4740
ccggctggct ggtttattgc tgataaatct ggagccggtg agcgtgggtc tcgcggtatc    4800
attgcagcac tggggccaga tggtaagccc tcccgtatcg tagttatcta cacgacgggg    4860
agtcaggcaa ctatggatga acgaaataga cagatcgctg agataggtgc ctcactgatt    4920
aagcattggt aactgtcaga ccaagtttac tcatatatac tttagattga tttaaaactt    4980
catttttaat ttaaaaggat ctaggtgaag atcctttttg ataatctcat gaccaaaatc    5040
ccttaacgtg agttttcgtt ccactgagcg tcagacccog tagaaaagat caaaggatct    5100
tcttgagatc ctttttttct gcgcgtaatc tgctgcttgc aaacaaaaaa accaccgcta    5160
ccagcggtgg tttgtttgcc ggatcaagag ctaccaactc tttttccgaa ggtaactggc    5220
```

```
ttcagcagag cgcagatacc aaatactgtc cttctagtgt agccgtagtt aggccaccac    5280
ttcaagaact ctgtagcacc gcctacatac ctcgctctgc taatcctgtt accagtggct    5340
gctgccagtg gcgataagtc gtgtcttacc gggttggact caagacgata gttaccggat    5400
aaggcgcagc ggtcgggctg aacgggggt tcgtgcacac agcccagctt ggagcgaacg     5460
acctacaccg aactgagata cctacagcgt gagctatgag aaagcgccac gcttcccgaa    5520
gggagaaagg cggacaggta tccggtaagc ggcagggtcg gaacaggaga gcgcacgagg    5580
gagcttccag ggggaaacgc ctggtatctt tatagtcctg tcgggtttcg ccacctctga    5640
cttgagcgtc gattttttgtg atgctcgtca gggggggcgga gcctatggaa aaacgccagc   5700
aacgcggcct ttttacggtt cctggccttt gctggcctt ttgctcacat gttctttcct     5760
gcgttatccc ctgattctgt ggataaccgt attaccgcct ttgagtgagc tgataccgct    5820
cgccgcagcc gaacgaccga gcgcagcgag tcagtgagcg aggaagcgga aga            5873
```

<210> SEQ ID NO 4
<211> LENGTH: 40
<212> TYPE: DNA
<213> ORGANISM: Artificial Sequence
<220> FEATURE:
<223> OTHER INFORMATION: primer CYP52A12_HYG-F

<400> SEQUENCE: 4

```
tcaagccaca cacgtcatcc gcatgcgaac ccgaaaatgg                            40
```

<210> SEQ ID NO 5
<211> LENGTH: 40
<212> TYPE: DNA
<213> ORGANISM: Artificial Sequence
<220> FEATURE:
<223> OTHER INFORMATION: primer CYP52A12_HYG-R

<400> SEQUENCE: 5

```
gatgtggtga tgggtgggct gctagcagct ggatttcact                            40
```

<210> SEQ ID NO 6
<211> LENGTH: 1776
<212> TYPE: DNA
<213> ORGANISM: Artificial Sequence
<220> FEATURE:
<223> OTHER INFORMATION: HYG

<400> SEQUENCE: 6

```
tcaagccaca cacgtcatcc gcatgcgaac ccgaaaatgg agcaatcttc cccggggcct      60
ccaaatacca actcacccga gagagataaa gagacaccac ccaccacgag acggagtata    120
tccaccaagg taagtaactc agagttaatg atacaggtgt acacagctcc ttccctagcc    180
attgagtggg tatcacatga cactggtagg ttacaaccac gtttagtagt tattttgtgc    240
aattccatgg ggatcaggaa gtttggtttg gtgggtgcgt ctactgattc ccctttgtct    300
ctgaaaatct tttccctagt ggaacacttt ggctgaatga tataaattca ccttgattcc    360
caccctccct tctttctctc tctctctgtt acacccaatt gaattttctt tttttttta     420 ctttccctcc ttctttatca tcaaagataa gtaagtttat caattgccta ttcagaatga    480
aaaagcctga actcaccgcg acgtctgtcg agaagtttct catcgaaaag ttcgacagcg    540
tctccgacct catgcagctc tcggagggcg aagaatctcg tgctttcagc ttcgatgtag    600
gagggcgtgg atatgtcctc cgggtaaata gctgcgccga tggtttctac aaagatcgtt    660
```

```
atgtttatcg gcactttgca tcggccgcgc tcccgattcc ggaagtgctt gacattgggg      720
aattcagcga gagcctcacc tattgcatct cccgccgtgc acagggtgtc acgttgcaag      780
acctccctga aaccgaactc cccgctgttc tccagccggt cgcggaggcc atggatgcga      840
tcgctgcggc cgatcttagc cagacgagcg ggttcggccc attcggaccg caaggaatcg      900
gtcaatacac tacatggcgt gatttcatat gcgcgattgc tgatccccat gtgtatcact      960
ggcaaactgt gatggacgac accgtcagtg cgtccgtcgc gcaggctctc gatgagctca     1020
tgctttgggc cgaggactgc cccgaagtcc ggcacctcgt gcacgcggat ttcggctcca     1080
acaatgtcct cacggacaat ggccgcataa cagcggtcat tgactggagc gaggcgatgt     1140
tcggggattc ccaatacgag gtcgccaaca tcttcttctg gaggccgtgg ttggcttgta     1200
tggagcagca gacgcgctac ttcgagcgga ggcatccgga gcttgcagga tcgccgcggc     1260
tccgggcgta tatgctccgc attggtcttg accaactcta tcagagcttg gttgacggca     1320
atttcgatga tgcagcttgg gcgcagggtc gatgcgacgc aatcgtccga tccggagccg     1380
ggactgtcgg gcgtacacaa atcgcccgca gaagcgcggc cgtctggacc gatggctgtg     1440
tagaagtact cgccgatagt ggaaaccgac gccccagcac tcgtccgagg gcaaaggaat     1500
agtgtgctac ccacgcttac tccaccagag ctattaacat cagaaatatt tattctaata     1560
aataggatgc aaaaaaaaaa ccccccttaa taaaaaaaaa agaaacgatt ttttatctaa     1620
tgaagtctat gtatctaaca aatgtatgta tcaatgttta ttccgttaaa caaaaatcag     1680
tctgtaaaaa aggttctaaa taaatattct gtctagtgta cacattctcc caaaatagtg     1740
aaatccagct gctagcagcc cacccatcac cacatc                               1776

<210> SEQ ID NO 7
<211> LENGTH: 20
<212> TYPE: DNA
<213> ORGANISM: Artificial Sequence
<220> FEATURE:
<223> OTHER INFORMATION: primer CYP52A12_Down-F

<400> SEQUENCE: 7
agcccaccca tcaccacatc                                                   20

<210> SEQ ID NO 8
<211> LENGTH: 20
<212> TYPE: DNA
<213> ORGANISM: Artificial Sequence
<220> FEATURE:
<223> OTHER INFORMATION: primer CYP52A12_Down-R

<400> SEQUENCE: 8
cgaagtcgta atccgcaacg                                                   20

<210> SEQ ID NO 9
<211> LENGTH: 253
<212> TYPE: DNA
<213> ORGANISM: Artificial Sequence
<220> FEATURE:
<223> OTHER INFORMATION: CYP52A12_Down

<400> SEQUENCE: 9
agcccaccca tcaccacatc cctctactcg acaacgtcca agacggcga gttctggtgt       60 gcccggaaat cagccatccc ggccacatac aagcagccgt tgattgcgtg catactcggc      120
gagcccacaa tgggagccac gcattcggac catgaagcaa agtacattca cgagatcacg      180
```

```
ggtgtttcag tgtcgcagat tgagaagttc gacgatggat ggaagtacga tctcgttgcg    240
gattacgact tcg                                                        253

<210> SEQ ID NO 10
<211> LENGTH: 4255
<212> TYPE: DNA
<213> ORGANISM: Artificial Sequence
<220> FEATURE:
<223> OTHER INFORMATION: fragment for homologous recombination

<400> SEQUENCE: 10
caaaacagca ctccgcttgt cacaggttgt ctcctctcaa ccaacaaaaa aataagatta     60
aactttcttt gctcatgcat caatcggagt tatctctgaa agagttgcct ttgtgtaatg    120
tgtgccaaac tcaaactgca aaactaacca cagaatgatt ccctcacaa ttatataaac     180 tcacccacat ttccacagac cgtaatttca tgtctcactt tctcttttgc tcttctttta    240
cttagtcagg tttgataact tccttttta ttacccctatc ttatttattt atttattcat    300
ttataccaac caaccaacca tggccacaca agaaatcatc gattctgtac ttccgtactt    360
gaccaaatgg tacactgtga ttactgcagc agtattagtc ttccttatct ccacaaacat    420
caagaactac gtcaaggcaa agaaattgaa atgtgtcgat ccaccatact gaaggatgc     480 cggtctcact ggtattctgt ctttgatcgc cgccatcaag gccaagaacg acggtagatt    540
ggctaacttt gccgatgaag ttttcgacga gtacccaaac cacaccttct acttgtctgt    600
tgccggtgct ttgaagattg tcatgactgt tgacccagaa aacatcaagg ctgtcttggc    660
cacccaattc actgacttct ccttgggtac cagacacgcc cactttgctc ctttgttggg    720
tgacggtatc ttcaccttgg acggagaagg ttggaagcac tccagagcta tgttgagacc    780
acagtttgct agagaccaga ttggacacgt taaagccttg gaaccacaca tccaaatcat    840
ggctaagcag atcaagttga accagggaaa gactttcgat atccaagaat tgttctttag    900
atttaccgtc gacaccgcta ctgagttctt gtttggtgaa tccgttcact ccttgtacga    960
tgaaaaattg ggcatcccaa ctccaaaacga atcccagga agagaaaact ttgccgctgc   1020
tttcaacgtt tccaacact acttggccac cagaagttac tcccagactt tttacttttt   1080 gaccaacccct aaggaattca gagactgtaa cgccaaggtc caccacttgg ccaagtactt   1140
tgtcaacaag gccttgaact ttactcctga agaactcgaa gagaaatcca gtccggtta    1200 cgttttcttg tacgaattgg ttaagcaaac cagagatcca aggtcttgc aagatcaatt   1260 gttgaacatt atggttgccg gaagagacac cactgccggt ttgttgtcct ttgctttgtt   1320
tgaattggct agacacccag agatgtggtc caagttgaga aagaaatcg aagttaactt    1380 tggtgttggt gaagactccc gcgttgaaga aattaccttc gaagccttga agagatgtga   1440
atacttgaag gctatcctta acgaaacctt gcgtatgtac ccatctgttc ctgtcaactt    1500
tagaaccgcc accagagaca ccactttgcc aagaggtggt ggtgctaacg gtaccgaccc   1560
aatctacatt cctaaaggct ccactgttgc ttacgttgtc tacaagaccc accgtttgga   1620
agaatactac ggtaaggacg ctaacgactt cagaccagaa agatggtttg aaccatctac   1680
taagaagttg ggctgggctt atgttccatt caacggtggt ccaagagtct gcttgggtca   1740
acaattcgcc ttgactgaag cttcttatgt gatcactaga ttggcccaga tgtttgaaac   1800
tgtctcatct gatccaggtc tcgaataccc tccaccaaag tgtattcact tgaccatgag   1860
tcacaacgat ggtgtctttg tcaagatgta aagtagtcga tgctgggtat tcgattacat   1920
```

```
gtgtatagga agattttggt tttttattcg ttcttttttt taattttttgt taaattagtt    1980
tagagatttc attaatacat agatgggtgc tatttccgaa acttacttc tatccctgt       2040
atcccttatt atccctctca gtcacatgat tgctgtaatt gtcgtgcagg acacaaactc    2100
cctaacggac ttaaaccata aacaagctca gaaccataag ccgacatcac tccttcttct    2160
ctcttctcca accaatagca tggacagacc caccctccta tccgaatcga agacccttat    2220
tgactccata cccacctgga agccctcaa gccacacacg tcatccgcat gcgaacccga     2280
aaatggagca atcttccccg gggcctccaa ataccaactc acccgagaga gataaagaga    2340
caccacccac cacgagacgg agtatatcca ccaaggtaag taactcagag ttaatgatac    2400
aggtgtacac agctccttcc ctagccattg agtgggtatc acatgacact ggtaggttac    2460
aaccacgttt agtagttatt ttgtgcaatt ccatggggat caggaagttt ggtttggtgg    2520
gtgcgtctac tgattcccct ttgtctctga aaatcttttc cctagtggaa cactttggct    2580
gaatgatata aattcacctt gattcccacc ctcccttctt tctctctctc tctgttacac    2640
ccaattgaat tttcttttt tttttacttt ccctccttct ttatcatcaa agataagtaa     2700
gtttatcaat tgcctattca gaatgaaaaa gcctgaactc accgcgacgt ctgtcgagaa    2760
gtttctcatc gaaaagttcg acagcgtctc cgacctcatg cagctctcgg agggcgaaga   2820
atctcgtgct ttcagcttcg atgtaggagg cgtggatat gtcctccggg taaatagctg     2880
cgccgatggt ttctacaaag atcgttatgt ttatcggcac tttgcatcgg ccgcgctccc    2940
gattccggaa gtgcttgaca ttggggaatt cagcgagagc ctcacctatt gcatctcccg    3000
ccgtgcacag ggtgtcacgt tgcaagacct ccctgaaacc gaactccccg ctgttctcca    3060
gccggtcgcg gaggccatgg atgcgatcgc tgcggccgat cttagccaga cgagcgggtt    3120
cggcccattc ggaccgcaag gaatcggtca atacactaca tggcgtgatt tcatatgcgc    3180
gattgctgat ccccatgtgt atcactggca aactgtgatg gacgacaccg tcagtgcgtc    3240
cgtcgcgcag gctctcgatg agctcatgct ttgggccgag gactgccccg aagtccggca    3300
cctcgtgcac gcggatttcg gctccaacaa tgtcctcacg gacaatggcc gcataacagc    3360
ggtcattgac tggagcgagg cgatgttcgg ggattcccaa tacgaggtcg ccaacatctt    3420
cttctggagg ccgtggttgg cttgtatgga gcagcagacg cgctacttcg agcggaggca    3480
tccggagctt gcaggatcgc cgcggctccg ggcgtatatg ctccgcattg gtcttgacca    3540
actctatcag agcttggttg acggcaattt cgatgatgca gcttgggcgc agggtcgatg    3600
cgacgcaatc gtccgatccg gagccgggac tgtcgggcgt acacaaatcg cccgcagaag    3660
cgcggccgtc tggaccgatg gctgtgtaga agtactcgcc gatagtggaa accgacgccc    3720
cagcactcgt ccgagggcaa aggaatagtg tgctacccac gcttactcca ccagagctat    3780
taacatcaga aatatttatt ctaataaata ggatgcaaaa aaaaaacccc ccttaataaa    3840
aaaaaagaa acgattttt atctaatgaa gtctatgtat ctaacaaatg tatgtatcaa      3900
tgtttattcc gttaaacaaa aatcagtctg taaaaaggt tctaaataaa tattctgtct     3960
agtgtacaca ttctcccaaa atagtgaaat ccagctgcta gcagcccacc catcaccaca    4020
tccctctact cgacaacgtc caaagacggc gagttctggt gtgcccggaa atcagccatc    4080
ccggccacat acaagcagcc gttgattgcg tgcatactcg gcgagcccac aatgggagcc    4140
acgcattcgg accatgaagc aaagtacatt cacgagatca cgggtgtttc agtgtcgcag    4200
attgagaagt tcgacgatgg atggaagtac gatctcgttg cggattacga cttcg          4255
```

<210> SEQ ID NO 11
<211> LENGTH: 1572
<212> TYPE: DNA
<213> ORGANISM: Artificial Sequence
<220> FEATURE:
<223> OTHER INFORMATION: mutant gene

<400> SEQUENCE: 11

```
atggccacac aagaaatcat cgattctgta cttccgtact tgaccaaatg gtacactgtg      60
attactgcag cagtattagt cttccttatc tccacaaaca tcaagaacta cgtcaaggca     120
aagaaattga atgtgtcga tccaccatac ttgaaggatg ccggtctcac tggtattctg     180
tctttgatcg ccgccatcaa ggccaagaac gacggtagat tggctgactt tgccgatgaa     240
gttttcgacg agtacccaaa ccacaccttc tacttgtctg ttgccggtgc tttgaagatt     300
gtcatgactg ttgacccaga aaacatcaag gctgtcttgg ccacccaatt cactgacttc     360
tccttgggta ccagacacgc ccactttgct cctttgttgg gtgacggtat cttcaccttg     420
gacggagaag gttggaagca ctccagagct atgttgagac acagtttgc tagagaccag     480
attggacacg ttaaagcctt ggaaccacac atccaaatca tggctaagca gatcaagttg     540
aaccagggaa agactttcga tatccaagaa ttgttcttta gatttaccgt cgacaccgct     600
actgagttct tgtttggtga atccgttcac tccttgtacg atgaaaaatt gggcatccca     660
actccaaacg aaatcccagg aagagaaaac tttgccgctg ctttcaacgt tcccaacac     720
tacttggcca ccagaagtta ctcccagact ttttactttt tgaccaaccc taaggaattc     780
agagactgta cgccaaggt ccaccacttg gccaagtact tgtcaacaa ggccttgaac     840
tttactcctg aagaactcga agagaaatcc aagtccggtt acgttttctt gtacgaattg     900
gttaagcaaa ccagagatcc aaaggtcttg caagatcaat tgttgaacat tatggttgca     960
ggaagagaca ccactgccgg tttgttgtcc tttgctttgt tgaattggc tagacaccca    1020
gagatgtggt ccaagttgag agaagaaatc gaagttaact ttggtgttgg tgaagactcc    1080
cgcgttgaag aaattacctt cgaagccttg aagagatgtg aatacttgaa ggctatcctt    1140
aacgaaacct tgcgtatgta cccatctgtt cctgtcaact ttagaaccgc caccagagac    1200
accactttgc caagaggtgg tggtgctaac ggtaccgacc aatctacat tcctaaaggc    1260
tccactgttg cttacgttgt ctacaagacc caccgtttgg aagaatacta cggtaaggac    1320
gctaacgact tcagaccaga aagatggttt gaaccatcta ctaagaagtt gggctgggct    1380
tatgttccat tcaacggtgg tccaagaatc tgcttgggtc aacaattcgc cttgactgaa    1440
gcttcttatg tgatcactag attggcccag atgtttgaaa ctgtctcatc tgatccaggt    1500
ctcgaatacc ctccaccaaa gtgtattcac ttgaccatga gtcacaacga tggtgtcttt    1560
gtcaagatgt aa                                                       1572
```

<210> SEQ ID NO 12
<211> LENGTH: 436
<212> TYPE: DNA
<213> ORGANISM: Artificial Sequence
<220> FEATURE:
<223> OTHER INFORMATION: gene with the resistance gene removed

<400> SEQUENCE: 12

```
gtgcaggaca caaactccct aacggactta aaccataaac aagctcagaa ccataagccg      60
acatcactcc ttcttctctc ttctccaacc aatagcatgg acagacccac cctcctatcc     120
gaatcgaaga cccttattga ctccataccc acctggaagc ccctcaagcc acacacgtca     180
```

```
tccagcccac ccatcaccac atccctctac tcgacaacgt ccaaagacgg cgagttctgg       240
tgtgcccgga aatcagccat cccggccaca tacaagcagc cgttgattgc gtgcatactc       300
ggcgagccca caatgggagc cacgcattcg gaccatgaag caaagtacat tcacgagatc       360
acgggtgttt cagtgtcgca gattgagaag ttcgacgatg gatggaagta cgatctcgtt       420
gcggattacg acttcg                                                       436

<210> SEQ ID NO 13
<211> LENGTH: 20
<212> TYPE: DNA
<213> ORGANISM: Artificial Sequence
<220> FEATURE:
<223> OTHER INFORMATION: primer CYP52A12_Ter-F

<400> SEQUENCE: 13
gtgcaggaca caaactccct                                                    20

<210> SEQ ID NO 14
<211> LENGTH: 20
<212> TYPE: DNA
<213> ORGANISM: Artificial Sequence
<220> FEATURE:
<223> OTHER INFORMATION: primer CYP52A12_Down-R

<400> SEQUENCE: 14
cgaagtcgta atccgcaacg                                                    20

<210> SEQ ID NO 15
<211> LENGTH: 20
<212> TYPE: DNA
<213> ORGANISM: Artificial Sequence
<220> FEATURE:
<223> OTHER INFORMATION: primer HYG-F

<400> SEQUENCE: 15
ctcggagggc gaagaatctc                                                    20

<210> SEQ ID NO 16
<211> LENGTH: 20
<212> TYPE: DNA
<213> ORGANISM: Artificial Sequence
<220> FEATURE:
<223> OTHER INFORMATION: primer HYG-R

<400> SEQUENCE: 16
caatgaccgc tgttatgcgg                                                    20

<210> SEQ ID NO 17
<211> LENGTH: 20
<212> TYPE: DNA
<213> ORGANISM: Artificial Sequence
<220> FEATURE:
<223> OTHER INFORMATION: primer CYP52A12-F

<400> SEQUENCE: 17
caaaacagca ctccgcttgt                                                    20

<210> SEQ ID NO 18
<211> LENGTH: 3936
<212> TYPE: DNA
<213> ORGANISM: Artificial Sequence
<220> FEATURE:
<223> OTHER INFORMATION: DNA fragment containing mutant CYP52A12 and HYG
      resistance genes
```

`<400> SEQUENCE: 18`

```
atggccacac aagaaatcat cgattctgta cttccgtact tgaccaaatg gtacactgtg     60
attactgcag cagtattagt cttccttatc tccacaaaca tcaagaacta cgtcaaggca    120
aagaaattga aatgtgtcga tccaccatac ttgaaggatg ccggtctcac tggtattctg    180
tctttgatcg ccgccatcaa ggccaagaac gacggtagat tggctaactt tgccgatgaa    240
gttttcgacg agtacccaaa ccacaccttc tacttgtctg ttgccggtgc tttgaagatt    300
gtcatgactg ttgacccaga aaacatcaag gctgtcttgg ccacccaatt cactgacttc    360
tccttgggta ccagacacgc ccactttgct cctttgttgg gtgacggtat cttcaccttg    420
gacggagaag gttggaagca ctccagagct atgttgagac acagtttgc tagagaccag     480
attggacacg ttaaagcctt ggaaccacac atccaaatca tggctaagca gatcaagttg    540
aaccagggaa agactttcga tatccaagaa ttgttcttta gatttaccgt cgacaccgct    600
actgagttct tgtttggtga atccgttcac tccttgtacg atgaaaaatt gggcatccca    660
actccaaacg aaatcccagg aagagaaaac tttgccgctg ctttcaacgt tcccaacac    720
tacttggcca ccagaagtta ctcccagact ttttactttt tgaccaaccc taaggaattc    780
agagactgta acgccaaggt ccaccacttg gccaagtact tgtcaacaa ggccttgaac     840
tttactcctg aagaactcga agagaaatcc aagtccggtt acgttttctt gtacgaattg    900
gttaagcaaa ccagagatcc aaaggtcttg caagatcaat tgttgaacat tatggttgcc    960
ggaagagaca ccactgccgg tttgttgtcc tttgctttgt ttgaattggc tagacaccca   1020
gagatgtggt ccaagttgag agaagaaatc gaagttaact tggtgttgg tgaagactcc    1080
cgcgttgaag aaattacctt cgaagccttg aagagatgtg aatacttgaa ggctatcctt   1140
aacgaaacct tgcgtatgta cccatctgtt cctgtcaact ttagaaccgc caccagagac   1200
accactttgc caagaggtgg tggtgctaac ggtaccgacc caatctacat tcctaaaggc   1260
tccactgttg cttacgttgt ctacaagacc accgttgg aagaatacta cggtaaggac      1320
gctaacgact tcagaccaga aagatggttt gaaccatcta ctaagaagtt gggctgggct   1380
tatgttccat tcaacggtgg tccaagagtc tgcttgggtc aacaattcgc cttgactgaa   1440
gcttcttatg tgatcactag attggcccag atgtttgaaa ctgtctcatc tgatccaggt   1500
ctcgaatacc ctccaccaaa gtgtattcac ttgaccatga gtcacaacga tggtgtcttt   1560
gtcaagatgt aaagtagtcg atgctgggta ttcgattaca tgtgtatagg aagattttgg   1620
tttttttattc gttctttttt ttaatttttg ttaaattagt ttagagattt cattaataca   1680
tagatgggtg ctatttccga aactttactt ctatcccctg tatcccttat tatccctctc   1740
agtcacatga ttgctgtaat tgtcgtgcag gacacaaact ccctaacgga cttaaaccat   1800
aaacaagctc agaaccataa gccgacatca ctccttcttc tctcttctcc aaccaatagc   1860
atggacagac ccaccctcct atccgaatcg aagaccctta ttgactccat acccacctgg   1920
aagcccctca agccacacac gtcatccgca tgcgaacccg aaaatggagc aatcttcccc   1980
ggggcctcca ataccaact cacccgagag agataaagag acaccaccca ccacgagacg     2040
gagtatatcc accaaggtaa gtaactcaga gttaatgata caggtgtaca cagctccttc   2100
cctagccatt gagtgggtat cacatgacac tggtaggtta caaccacgtt tagtagttat    2160
tttgtgcaat tccatgggga tcaggaagtt tggtttggtg ggtgcgtcta ctgattcccc   2220
tttgtctctg aaaatctttt ccctagtgga acactttggc tgaatgatat aaattcacct   2280
tgattcccac cctcccttct ttctctctct ctctgttaca cccaattgaa ttttctttt    2340
```

```
tttttttactt tccctccttc tttatcatca aagataagta agtttatcaa ttgcctattc    2400
agaatgaaaa agcctgaact caccgcgacg tctgtcgaga agtttctcat cgaaaagttc    2460
gacagcgtct ccgacctcat gcagctctcg gagggcgaag aatctcgtgc tttcagcttc    2520
gatgtaggag ggcgtggata tgtcctccgg gtaaatagct gcgccgatgg tttctacaaa    2580
gatcgttatg tttatcggca ctttgcatcg gccgcgctcc cgattccgga agtgcttgac    2640
attggggaat tcagcgagag cctcacctat tgcatctccc gccgtgcaca gggtgtcacg    2700
ttgcaagacc tccctgaaac cgaactcccc gctgttctcc agccggtcgc ggaggccatg    2760
gatgcgatcc tgcggccga tcttagccag acgagcgggt tcggcccatt cggaccgcaa    2820
ggaatcggtc aatacactac atggcgtgat ttcatatgcg cgattgctga tccccatgtg    2880
tatcactggc aaactgtgat ggacgacacc gtcagtgcgt ccgtcgcgca ggctctcgat    2940
gagctcatgc tttgggccga ggactgcccc gaagtccggc acctcgtgca cgcggatttc    3000
ggctccaaca atgtcctcac ggacaatggc cgcataacag cggtcattga ctggagcgag    3060
gcgatgttcg gggattccca atacgaggtc gccaacatct tcttctggag gccgtggttg    3120
gcttgtatgg agcagcagac gcgctacttc gagcggaggc atccggagct tgcaggatcg    3180
ccgcggctcc gggcgtatat gctccgcatt ggtcttgacc aactctatca gagcttggtt    3240
gacggcaatt tcgatgatgc agcttgggcg caggtcgat gcgacgcaat cgtccgatcc    3300
ggagccggga ctgtcgggcg tacacaaatc gcccgcagaa gcgcggccgt ctggaccgat    3360
ggctgtgtag aagtactcgc cgatagtgga accgacgcc ccagcactcg tccgagggca    3420
aaggaatagt gtgctaccca cgcttactcc accagagcta ttaacatcag aaatatttat    3480
tctaataaat aggatgcaaa aaaaaaaccc cccttaataa aaaaaaaga acgattttt    3540 tatctaatga agtctatgta tctaacaaat gtatgtatca atgtttattc cgttaaacaa    3600
aaatcagtct gtaaaaaagg ttctaaataa atattctgtc tagtgtacac attctcccaa    3660
aatagtgaaa tccagctgct agcagcccac ccatcaccac atccctctac tcgacaacgt    3720
ccaaagacgg cgagttctgg tgtgcccgga aatcagccat cccggccaca tacaagcagc    3780
cgttgattgc gtgcatactc ggcgagccca caatgggagc cacgcattcg gaccatgaag    3840
caaagtacat tcacgagatc acgggtgttt cagtgtcgca gattgagaag ttcgacgatg    3900
gatggaagta cgatctcgtt gcggattacg acttcg                              3936
```

<210> SEQ ID NO 19
<211> LENGTH: 4115
<212> TYPE: DNA
<213> ORGANISM: Candida tropicalis

<400> SEQUENCE: 19

```
catatgcgct aatcttcttt ttctttttat cacaggagaa actatcccac ccccacttcg     60
aaacacaatg acaactcctg cgtaacttgc aaattcttgt ctgactaatt gaaaactccg    120
gacgagtcag acctccagtc aaacggacag acagacaaac acttggtgcg atgttcatac    180
ctacagacat gtcaacgggt gttagacgac ggtttcttgc aaagacaggt gttggcatct    240
cgtacgatgg caactgcagg aggtgtcgac ttctcccttta ggcaatagaa aaagactaag    300
agaacagcgt ttttacaggt tgcattggtt aatgtagtat ttttttagtc ccagcattct    360
gtgggttgct ctgggtttct agaataggaa atcacaggag aatgcaaatt cagatggaag    420
aacaaagaga taaaaaacaa aaaaaaactg agttttgcac caatagaatg tttgatgata    480
```

```
tcatccactc gctaaacgaa tcatgtgggt gatcttctct ttagttttgg tctatcataa      540
aacacatgaa agtgaaatcc aaatacacta cactccgggt attgtccttc gttttacaga      600
tgtctcattg tcttactttt gaggtcatag gagttgcctg tgagagatca cagagattat      660
cacactcaca tttatcgtag tttcctatct catgctgtgt gtctctggtt ggttcatgag      720
tttggattgt tgtacattaa aggaatcgct ggaaagcaaa gctaactaaa ttttctttgt      780
cacaggtaca ctaacctgta aaacttcact gccacgccag tctttcctga ttgggcaagt      840
gcacaaacta caacctgcaa aacagcactc cgcttgtcac aggttgtctc ctctcaacca      900
acaaaaaaat aagattaaac tttctttgct catgcatcaa tcggagttat ctctgaaaga      960
gttgcctttg tgtaatgtgt gccaaactca aactgcaaaa ctaaccacag aatgatttcc     1020
ctcacaatta tataaactca cccacatttc cacagaccgt aatttcatgt ctcactttct     1080
cttttgctct tcttttactt agtcaggttt gataacttcc ttttttatta ccctatctta     1140
tttatttatt tattcattta taccaaccaa ccaaccatgg ccacacaaga aatcatcgat     1200
tctgtacttc cgtacttgac caaatggtac actgtgatta ctgcagcagt attagtcttc     1260
cttatctcca caaacatcaa gaactacgtc aaggcaaaga aattgaaatg tgtcgatcca     1320
ccatacttga aggatgccgg tctcactggt attctgtctt tgatcgccgc catcaaggcc     1380
aagaacgacg gtagattggc taactttgcc gatgaagttt tcgacgagta cccaaaccac     1440
accttctact tgtctgttgc cggtgctttg aagattgtca tgactgttga cccagaaaac     1500
atcaaggctg tcttggccac ccaattcact gacttctcct tgggtaccag acacgcccac     1560
tttgctcctt tgtgggtgag cggtatcttc accttggacg gagaaggttg gaagcactcc     1620
agagctatgt tgagaccaca gtttgctaga gaccagattg gacacgttaa agccttggaa     1680
ccacacatcc aaatcatggc taagcagatc aagttgaacc agggaaagac tttcgatatc     1740
caagaattgt tctttagatt taccgtcgac accgctactg agttcttgtt tggtaatcc      1800 gttcactcct tgtacgatga aaaattgggc atcccaactc caaacgaaat cccaggaaga     1860
gaaaactttg ccgctgcttt caacgtttcc caacactact tggccaccag aagttactcc     1920 cagactttt actttttgac caaccctaag gaattcagag actgtaacgc caaggtccac     1980
cacttggcca agtactttgt caacaaggcc ttgaacttta ctcctgaaga actcgaagag     2040
aaatccaagt ccggttacgt tttcttgtac gaattggtta agcaaaccag agatccaaag     2100
gtcttgcaag atcaattgtt gaacattatg gttgccggaa gagacaccac tgccggtttg     2160
ttgtcctttg ctttgtttga attggctaga cacccagaga tgtggccaa gttgagagaa     2220 gaaatcgaag ttaactttgg tgttggtgaa gactcccgcg ttgaagaaat taccttcgaa     2280
gccttgaaga gatgtgaata cttgaaggct atccttaacg aaaccttgcg tatgtaccca     2340
tctgttcctg tcaactttag aaccgccacc agagacacca ctttgccaag aggtggtggt     2400
gctaacggta ccgacccaat ctacattcct aaaggctcca ctgttgctta cgttgtctac     2460
aagacccacc gtttggaaga atactacggt aaggacgcta acgacttcag accagaaaga     2520
tggtttgaac catctactaa gaagttgggc tgggcttatg ttccattcaa cggtggtcca     2580
agagtctgct tgggtcaaca attcgccttg actgaagctt cttatgtgat cactagattg     2640
gcccagatgt ttgaaactgt ctcatctgat ccaggtctcg aatacctcc accaaagtgt     2700 attcacttga ccatgagtca caacgatggt gtctttgtca agatgtaaag tagtcgatgc     2760
tgggtattcg attacatgtg tataggaaga ttttggtttt ttattcgttc ttttttttaa     2820
tttttgttaa attagtttag agatttcatt aatacataga tgggtgctat ttccgaaact     2880
```

-continued

```
ttacttctat cccctgtatc ccttattatc cctctcagtc acatgattgc tgtaattgtc    2940
gtgcaggaca caaactccct aacggactta aaccataaac aagctcagaa ccataagccg    3000
acatcactcc ttcttctctc ttctccaacc aatagcatgg acagacccac cctcctatcc    3060
gaatcgaaga cccttattga ctccataccc acctggaagc ccctcaagcc acacacgtca    3120
tccagcccac ccatcaccac atccctctac tcgacaacgt ccaaagacgg cgagttctgg    3180
tgtgcccgga aatcagccat cccggccaca tacaagcagc cgttgattgc gtgcatactc    3240
ggcgagccca caatgggagc cacgcattcg gaccatgaag caaagtacat tcacgagatc    3300
acgggtgttt cagtgtcgca gattgagaag ttcgacgatg gatggaagta cgatctcgtt    3360
gcggattacg acttcggtgg gttgttatct aaacgaagat tctatgagac gcagcatgtg    3420
tttcggttcg aggattgtgc gtacgtcatg agtgtgcctt tgatggacc caaggaggaa    3480 ggttacgtgg ttgggacgta cagatccatt gaaaggttga gctggggtaa agacggggac    3540
gtggagtgga ccatggcgac gacgtcggat cctggtgggt tatcccgca atggataact    3600 cgattgagca tccctggagc aatcgcaaaa gatgtgccta gtgtattaaa ctacatacag    3660
aaataaaaac gtgtcttgat tcattggttt ggttcttgtt gggttccgag ccaatatttc    3720
acatcatctc ctaaattctc caagaatccc aacgtagcgt agtccagcac gccctctgag    3780
atcttattta atatcgactt ctcaaccacc ggtggaatcc cgttcagacc attgttacct    3840
gtagtgtgtt tgctcttgtt cttgatgaca atgatgtatt tgtcacgata cctgaaataa    3900
taaaacatcc agtcattgag cttattactc gtgaacttat gaaagaactc attcaagccg    3960
ttcccaaaaa acccagaatt gaagatcttg ctcaactggt catgcaagta gtagatcgcc    4020
atgatctgat actttaccaa gctatcctct ccaagttctc ccacgtacgg caagtacggc    4080
aacgagctct ggaagctttg ttgtttgggg tcata                              4115
```

<210> SEQ ID NO 20
<211> LENGTH: 523
<212> TYPE: PRT
<213> ORGANISM: Candida tropicalis
<220> FEATURE:
<221> NAME/KEY: PEPTIDE
<222> LOCATION: (1)..(523)

<400> SEQUENCE: 20

```
Met Ala Thr Gln Glu Ile Ile Asp Ser Val Leu Pro Tyr Leu Thr Lys
1               5                   10                  15

Trp Tyr Thr Val Ile Thr Ala Ala Val Leu Val Phe Leu Ile Ser Thr
            20                  25                  30

Asn Ile Lys Asn Tyr Val Lys Ala Lys Lys Leu Lys Cys Val Asp Pro
        35                  40                  45

Pro Tyr Leu Lys Asp Ala Gly Leu Thr Gly Ile Ser Ser Leu Ile Ala
    50                  55                  60

Ala Ile Lys Ala Lys Asn Asp Gly Arg Leu Ala Asn Phe Ala Asp Glu
65                  70                  75                  80

Val Phe Asp Glu Tyr Pro Asn His Thr Phe Tyr Leu Ser Val Ala Gly
                85                  90                  95

Ala Leu Lys Ile Val Met Thr Val Asp Pro Glu Asn Ile Lys Ala Val
            100                 105                 110

Leu Ala Thr Gln Phe Thr Asp Phe Ser Leu Gly Thr Arg His Ala His
        115                 120                 125
```

Phe Ala Pro Leu Leu Gly Asp Gly Ile Phe Thr Leu Asp Gly Glu Gly
        130                 135                 140

Trp Lys His Ser Arg Ala Met Leu Arg Pro Gln Phe Ala Arg Asp Gln
145                 150                 155                 160

Ile Gly His Val Lys Ala Leu Glu Pro His Ile Gln Ile Met Ala Lys
                165                 170                 175

Gln Ile Lys Leu Asn Gln Gly Lys Thr Phe Asp Ile Gln Glu Leu Phe
            180                 185                 190

Phe Arg Phe Thr Val Asp Thr Ala Thr Glu Phe Leu Phe Gly Glu Ser
        195                 200                 205

Val His Ser Leu Tyr Asp Glu Lys Leu Gly Ile Pro Thr Pro Asn Glu
    210                 215                 220

Ile Pro Gly Arg Glu Asn Phe Ala Ala Ala Phe Asn Val Ser Gln His
225                 230                 235                 240

Tyr Leu Ala Thr Arg Ser Tyr Ser Gln Thr Phe Tyr Phe Leu Thr Asn
                245                 250                 255

Pro Lys Glu Phe Arg Asp Cys Asn Ala Lys Val His His Leu Ala Lys
            260                 265                 270

Tyr Phe Val Asn Lys Ala Leu Asn Phe Thr Pro Glu Glu Leu Glu Glu
        275                 280                 285

Lys Ser Lys Ser Gly Tyr Val Phe Leu Tyr Glu Leu Val Lys Gln Thr
    290                 295                 300

Arg Asp Pro Lys Val Leu Gln Asp Gln Leu Leu Asn Ile Met Val Ala
305                 310                 315                 320

Gly Arg Asp Thr Thr Ala Gly Leu Leu Ser Phe Ala Leu Phe Glu Leu
                325                 330                 335

Ala Arg His Pro Glu Met Trp Ser Lys Leu Arg Glu Glu Ile Glu Val
            340                 345                 350

Asn Phe Gly Val Gly Glu Asp Ser Arg Val Glu Glu Ile Thr Phe Glu
        355                 360                 365

Ala Leu Lys Arg Cys Glu Tyr Leu Lys Ala Ile Leu Asn Glu Thr Leu
    370                 375                 380

Arg Met Tyr Pro Ser Val Pro Val Asn Phe Arg Thr Ala Thr Arg Asp
385                 390                 395                 400

Thr Thr Leu Pro Arg Gly Gly Ala Asn Gly Thr Asp Pro Ile Tyr
                405                 410                 415

Ile Pro Lys Gly Ser Thr Val Ala Tyr Val Val Tyr Lys Thr His Arg
            420                 425                 430

Leu Glu Glu Tyr Tyr Gly Lys Asp Ala Asn Asp Phe Arg Pro Glu Arg
        435                 440                 445

Trp Phe Glu Pro Ser Thr Lys Lys Leu Gly Trp Ala Tyr Val Pro Phe
    450                 455                 460

Asn Gly Gly Pro Arg Val Cys Leu Gly Gln Gln Phe Ala Leu Thr Glu
465                 470                 475                 480

Ala Ser Tyr Val Ile Thr Arg Leu Ala Gln Met Phe Glu Thr Val Ser
                485                 490                 495

Ser Asp Pro Gly Leu Glu Tyr Pro Pro Pro Lys Cys Ile His Leu Thr
            500                 505                 510

Met Ser His Asn Asp Gly Val Phe Val Lys Met
        515                 520

<210> SEQ ID NO 21
<211> LENGTH: 523

<212> TYPE: PRT
<213> ORGANISM: Artificial sequence
<220> FEATURE:
<223> OTHER INFORMATION: mutant CYP52A12 protein

<400> SEQUENCE: 21

Met Ala Thr Gln Glu Ile Ile Asp Ser Val Leu Pro Tyr Leu Thr Lys
1               5                   10                  15

Trp Tyr Thr Val Ile Thr Ala Val Leu Val Phe Leu Ile Ser Thr
            20                  25                  30

Asn Ile Lys Asn Tyr Val Lys Ala Lys Lys Leu Lys Cys Val Asp Pro
        35                  40                  45

Pro Tyr Leu Lys Asp Ala Gly Leu Thr Gly Ile Ser Ser Leu Ile Ala
    50                  55                  60

Ala Ile Lys Ala Lys Asn Asp Gly Arg Leu Ala Asp Phe Ala Asp Glu
65                  70                  75                  80

Val Phe Asp Glu Tyr Pro Asn His Thr Phe Tyr Leu Ser Val Ala Gly
                85                  90                  95

Ala Leu Lys Ile Val Met Thr Val Asp Pro Glu Asn Ile Lys Ala Val
            100                 105                 110

Leu Ala Thr Gln Phe Thr Asp Phe Ser Leu Gly Thr Arg His Ala His
        115                 120                 125

Phe Ala Pro Leu Leu Gly Asp Gly Ile Phe Thr Leu Asp Gly Glu Gly
130                 135                 140

Trp Lys His Ser Arg Ala Met Leu Arg Pro Gln Phe Ala Arg Asp Gln
145                 150                 155                 160

Ile Gly His Val Lys Ala Leu Glu Pro His Ile Gln Ile Met Ala Lys
                165                 170                 175

Gln Ile Lys Leu Asn Gln Gly Lys Thr Phe Asp Ile Gln Glu Leu Phe
            180                 185                 190

Phe Arg Phe Thr Val Asp Thr Ala Thr Glu Phe Leu Phe Gly Glu Ser
        195                 200                 205

Val His Ser Leu Tyr Asp Glu Lys Leu Gly Ile Pro Thr Pro Asn Glu
210                 215                 220

Ile Pro Gly Arg Glu Asn Phe Ala Ala Ala Phe Asn Val Ser Gln His
225                 230                 235                 240

Tyr Leu Ala Thr Arg Ser Tyr Ser Gln Thr Phe Tyr Phe Leu Thr Asn
                245                 250                 255

Pro Lys Glu Phe Arg Asp Cys Asn Ala Lys Val His His Leu Ala Lys
            260                 265                 270

Tyr Phe Val Asn Lys Ala Leu Asn Phe Thr Pro Glu Glu Leu Glu Glu
        275                 280                 285

Lys Ser Lys Ser Gly Tyr Val Phe Leu Tyr Glu Leu Val Lys Gln Thr
290                 295                 300

Arg Asp Pro Lys Val Leu Gln Asp Gln Leu Leu Asn Ile Met Val Ala
305                 310                 315                 320

Gly Arg Asp Thr Thr Ala Gly Leu Leu Ser Phe Ala Leu Phe Glu Leu
                325                 330                 335

Ala Arg His Pro Glu Met Trp Ser Lys Leu Arg Glu Glu Ile Glu Val
            340                 345                 350

Asn Phe Gly Val Gly Glu Asp Ser Arg Val Glu Glu Ile Thr Phe Glu
        355                 360                 365

Ala Leu Lys Arg Cys Glu Tyr Leu Lys Ala Ile Leu Asn Glu Thr Leu
370                 375                 380

```
Arg Met Tyr Pro Ser Val Pro Val Asn Phe Arg Thr Ala Thr Arg Asp
385                 390                 395                 400

Thr Thr Leu Pro Arg Gly Gly Gly Ala Asn Gly Thr Asp Pro Ile Tyr
            405                 410                 415

Ile Pro Lys Gly Ser Thr Val Ala Tyr Val Val Tyr Lys Thr His Arg
                420                 425                 430

Leu Glu Glu Tyr Tyr Gly Lys Asp Ala Asn Asp Phe Arg Pro Glu Arg
            435                 440                 445

Trp Phe Glu Pro Ser Thr Lys Lys Leu Gly Trp Ala Tyr Val Pro Phe
    450                 455                 460

Asn Gly Pro Arg Ile Cys Leu Gly Gln Gln Phe Ala Leu Thr Glu
465                 470                 475                 480

Ala Ser Tyr Val Ile Thr Arg Leu Ala Gln Met Phe Glu Thr Val Ser
                485                 490                 495

Ser Asp Pro Gly Leu Glu Tyr Pro Pro Pro Lys Cys Ile His Leu Thr
            500                 505                 510

Met Ser His Asn Asp Gly Val Phe Val Lys Met
        515                 520
```

<210> SEQ ID NO 22
<211> LENGTH: 1572
<212> TYPE: DNA
<213> ORGANISM: Candida tropicalis

<400> SEQUENCE: 22

```
atggccacac aagaaatcat cgattctgta cttccgtact tgaccaaatg gtacactgtg      60
attactgcag cagtattagt cttccttatc tccacaaaca tcaagaacta cgtcaaggca     120
aagaaattga atgtgtcga tccaccatac ttgaaggatg ccggtctcac tggtattctg     180
tctttgatcg ccgccatcaa ggccaagaac gacggtagat ggctaacttt gccgatgaa     240
gttttcgacg agtacccaaa ccacaccttc tacttgtctg ttgccggtgc tttgaagatt     300
gtcatgactg ttgacccaga aaacatcaag gctgtcttgg ccacccaatt cactgacttc     360
tccttgggta ccagacacgc ccactttgct cctttgttgg gtgacggtat cttcaccttg     420
gacggagaag gttggaagca ctccagagct atgttgagac acagtttgc tagagaccag     480
attggacacg ttaaagcctt ggaaccacac atccaaatca tggctaagca gatcaagttg     540
aaccagggaa agactttcga tatccaagaa ttgttcttta gatttaccgt cgacaccgct     600
actgagttct gtttggtga atccgttcac tccttgtacg atgaaaaatt gggcatccca     660
actccaaacg aaatcccagg aagagaaaac tttgccgctg ctttcaacgt tcccaacac     720
tacttggcca ccagaagtta ctcccagact ttttactttt tgaccaaccc taaggaattc     780
agagactgta acgccaaggt ccaccacttg gccaagtact tgtcaacaa ggccttgaac     840
tttactcctg aagaactcga agagaaatcc aagtccggtt acgtttcttt gtacgaattg     900
gttaagcaaa ccagagatcc aaaggtcttg caagatcaat tgttgaacat tatggttgcc     960
ggaagagaca ccactgccgg tttgttgtcc tttgctttgt ttgaattggc tagacaccca    1020
gagatgtggt ccaagttgag agaagaaatc gaagttaact tggtgttgg tgaagactcc    1080
cgcgttgaag aaattacctt cgaagccttg aagagatgtg aatacttgaa ggctatcctt    1140
aacgaaacct tgcgtatgta cccatctgtt cctgtcaact ttagaaccgc accagagac    1200
accactttgc caagaggtgg tggtgctaac ggtaccgacc caatctacat tcctaaggc    1260
tccactgttg cttacgttgt ctacaagacc caccgtttgg aagaatacta cggtaaggac    1320
```

-continued

| | | | | | |
|---|---|---|---|---|---|
| gctaacgact | tcagaccaga | aagatggttt | gaaccatcta | ctaagaagtt | gggctgggct | 1380
| tatgttccat | tcaacggtgg | tccaagagtc | tgcttgggtc | aacaattcgc | cttgactgaa | 1440
| gcttcttatg | tgatcactag | attggcccag | atgtttgaaa | ctgtctcatc | tgatccaggt | 1500
| ctcgaatacc | ctccaccaaa | gtgtattcac | ttgaccatga | gtcacaacga | tggtgtcttt | 1560
| gtcaagatgt | aa | | | | | 1572

DIRECTED EVOLUTION OF CYP52A12 GENE AND ITS USE IN DICARBOXYLIC ACID PRODUCTION

FIELD OF THE INVENTION

The invention relates to a method of preparing a long chain dicarboxylic acid producing strain by using directed evolution and homologous recombination, a strain obtained by this method that is capable of producing a long chain dicarboxylic acid under an acidic condition and the use thereof. In particular, the invention relates to a method of preparing a long chain dicarboxylic acid producing strain by using directed evolution of CYP52A12 gene and homologous recombination, a strain obtained by this method that is capable of producing a long chain dicarboxylic acid under an acidic condition and the use thereof.

BACKGROUND

A long chain dicarboxylic acid (LCDA; also referred to as long chain diacid) is a diacid having the formula HOOC$(CH_2)_n$COOH, $n \geq 7$. As an important monomer raw material, long chain dicarboxylic acids are widely used in the synthesis of nylon, resin, hot-melt adhesive, powder coating, preservative, perfume, lubricant, plasticizer, and the like.

Long chain dicarboxylic acids have long been synthesized via petroleum by conventional chemical synthesis routes such as butadiene multi-step oxidation. However, the chemical synthesis faces many challenges. The dicarboxylic acids obtained by the chemical synthesis are a mixture of long chain dicarboxylic acids and short-chain dicarboxylic acids, and therefore subsequent complicated extraction and purification steps are required, which are huge obstacles for production processes and production costs. The production of a long chain dicarboxylic acid by microbial fermentation technology has apparent advantages than a conventional chemical synthesis because it produces less pollution, is environmentally friendly and is able to produce a product that is difficult to be synthesized through a chemical synthesis, such as a long chain dicarboxylic acid having a carbon number of 12 or higher, and the product has a high purity.

The biosynthesis of a dicarboxylic acid is based on the conversion of the substrate a long chain alkane by a microorganism such as *Candida*. Its production process is under a normal temperature and pressure, and it can produce C9 to C18 and other long chain dicarboxylic acids on a large scale. The current fermentation process relies on a high-pH alkaline environment. Published patent applications or patents such as CN1071951A, CN1067725C, CN1259424C, CN200410018255.7, CN200610029784.6 and the like require that the pH of the fermentation broth is adjusted to 7.0 or higher during the acid producing period due to the following reasons: 1) P450, a key enzyme in the dicarboxylic acid metabolic pathway of *Candida tropicalis*, has a high enzymatic activity in an alkaline environment; 2) the long chain dicarboxylic acid can present in its salt form dissolved in water under an alkaline condition, which allows good mass transfer during fermentation. In order to maintain the pH value of fermentation system above 7.0 during the acid producing period, a large amount of alkali is required to be added to neutralize the produced long chain dicarboxylic acid. The subsequent extraction and purification of the dicarboxylic acid requires a large amount of acid to convert the long chain dicarboxylic acid salt in the system into the long chain dicarboxylic acid, leading the concentration of salt up to 50-70 g/L in the acidified mother liquor system. The existence of high salt wastewater has brought great challenges to the environment, which seriously affects the development of the biosynthesis of a long chain dicarboxylic acid in industry.

U.S. Pat. No. 6,569,670B2 also disclosed a process of producing a long chain dicarboxylic acid with a fatty acid as raw material in an environment of pH 5.8, mainly because at a pH above 7.0, the fatty acid is present in the form of fatty acid salt, which foams easily, and the fermentation cannot be carried out. Therefore, the fermentation must be performed at a low pH. However, the activity of the P450 enzyme is lower at a low pH, the metabolism is slow, and the production efficiency is low.

Previously, the improvement of a dicarboxylic acid producing strain was mostly achieved through conventional random mutagenesis or genetic engineering. The main purpose of the modification is to increase the conversion rate of dicarboxylic acid. Due to the randomness of mutagenesis, there is a high requirement for screening throughput, and a new round of mutagenesis screening is required for each trait change, which has become an important limiting factor in technology. The genetic engineering can be used to produce a targeted genetic modification of a strain, so as to obtain a better strain with a higher yield. The production of a long chain dicarboxylic acid by microbial fermentation method is mainly via ω-oxidation of alkane, which can then be degraded via β-oxidation pathway. Previous studies have shown that the yield of a long chain dicarboxylic acid can be increased by means of enhancing the ω-oxidation pathway and inhibiting the β-oxidation pathway. Pictaggio et al. of Coginis (Mol. Cell. Biol., 11(9), 4333-4339, 1991) reported that knockout of two alleles of each POX4 and POX5 can effectively block the β-oxidation pathway to achieve 100% conversion of the substrate. Further overexpression of two key enzymes, P450 and oxidoreductase CYP52A12, in the rate-limiting step in the ω-oxidation pathway can effectively increase yield (Biotechnology, 10, 894-898, 1992). Lai, Xiaoqin et al. (Chinese patent CN103992959B) reported that the introduction of one copy of the CYP52A14 gene into a dicarboxylic acid-producing strain can also effectively increase the dicarboxylic acid conversion rate and production efficiency. In addition, Cao et al. (Biotechnol. J., 1, 68-74, 2006) found that knocking out a copy of the key gene CAT during the transportation of acetyl coenzyme A from peroxisome to mitochondria can partially block the acetyl coenzyme A from entering into the citric acid cycle, and can effectively reduce the degradation of a dicarboxylic acid.

Error-prone PCR is a technique proposed by Leung et al. (Technique, 1, 11-15, 1989) for constructing a gene library for directed studies. By changing the PCR reaction condition, such as adjusting the concentration of four deoxyribonucleic acids in the reaction system, changing the concentration of $Mg^{2+}$, and using a low-fidelity DNA polymerase and the like, a base mismatch is made so as to introduce a mutation. Too high or too low mutation rate will affect the effect of constructing a mutant library. An ideal base mutation ratio is 1-3 per DNA fragment. Therefore, the use of error-prone PCR to generate random mutations in combination with homologous recombination to make a directed genetic modification to a gene, can assist in screening out beneficial mutation(s) that contribute to the improvement of the strain productivity. Previously, the modification to a dicarboxylic acid producing strain focused on random mutagenesis or overexpression of a gene that is in the upstream synthesis pathway or on blocking downstream β-oxidation pathway. Directed evolution of a gene in the metabolic pathway has not been reported or applied.

It has not been reported that a method of directed evolution is used to modify a dicarboxylic acid producing strain to adapt it to an acidic fermentation condition. There is still a need in the art for a strain adapted to an acidic fermentation condition and the preparation method thereof.

SUMMARY OF THE INVENTION

In the first aspect, the invention relates to a mutant CYP52A12 gene, a homologous gene or a variant thereof, which has the following base mutations relative to the gene with Accession No. AY230498 in the GenBank (SEQ ID NO: 19), taking the first base of the start codon ATG (base 1177 of SEQ ID NO: 19) as 1: c.226A>G, c.960C>A, c.1408G>A; and wherein said variant has at least or at least about 70%, for example, at least or at least about 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, 99.91%, 99.92%, 99.93%, 99.94%, 99.95% or 99.96%, sequence identity with the mutant CYP52A12 gene or the homologous gene thereof.

In some embodiments, the sequence of said mutant CYP52A12 gene is set forth in SEQ ID NO: 10 or 11 or has at least or at least about 70%, for example, at least or at least about 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, 99.91%, 99.92%, 99.93%, 99.94%, 99.95% or 99.96%, sequence identity thereto.

In the second aspect, the invention relates to a microorganism containing the mutant CYP52A12 gene, a homologous gene or a variant thereof as provided in the first aspect, which is capable of producing a long chain dicarboxylic acid under an acidic culture condition, compared to a microorganism containing a non-mutant CYP52A12 gene or a homologous gene thereof. Preferably, said microorganism is selected from the group consisting of *Corynebacterium, Geotrichum candidum, Candida, Pichia, Rhodotroula, Saccharomyces* and *Yarrowia*; more preferably said microorganism is yeast, and more preferably said microorganism is *Candida tropicalis* or *Candida sake*. In one embodiment, the microorganism is the strain *Candida tropicalis* CCTCC M 2011192 or CCTCC M 203052 (deposited at China Center for Type Culture Collection).

In some embodiments, the long chain dicarboxylic acid is selected from the group consisting of C9-C22 long chain dicarboxylic acids, preferably C9-C18 long chain dicarboxylic acids, more preferably selected from one or more of sebacic acid, undecanedioic acid, dodecanedioic acid, tridecanedioic acid, tetradecanedioic acid, pentadecanedioic acid and hexadecanedioic acid, and more preferably the long chain dicarboxylic acid is at least one selected from C12 to C16 dicarboxylic acids or at least one selected from normal C12 to C16 dicarboxylic acids.

In some embodiments, the acidic culture condition refers to controlling the pH of the fermentation system to be 7.0 or lower, preferably 4.0 to 6.8, more preferably 5.0 to 6.5; and preferably controlling the pH of the fermentation system is controlling the pH of the fermentation system during the conversion period.

In the third aspect, the invention relates to a method for producing a long chain dicarboxylic acid using the microorganism according to the second aspect as provided above, comprising the step of culturing the microorganism according to the second aspect, and optionally further comprising the step of separating and purifying the long chain dicarboxylic acid from the cultured products.

In the fourth aspect, the invention relates to a method of modifying a long chain dicarboxylic acid producing strain by directed evolution of a key gene in the long chain dicarboxylic acid synthesis pathway, wherein the modified long chain dicarboxylic acid-producing strain is capable of producing the long chain dicarboxylic acid under an acidic culture condition compared to the strain before modified. Preferably, the key gene in the long chain dicarboxylic acid synthesis pathway is the gene CYP52A12.

In some embodiments, the long chain dicarboxylic acid is selected from the group consisting of C9-C22 long chain dicarboxylic acids, preferably C9-C18 long chain dicarboxylic acids, more preferably selected from one or more of sebacic acid, undecanedioic acid, dodecanedioic acid, tridecanedioic acid, tetradecanedioic acid, pentadecanedioic acid and hexadecanedioic acid, and more preferably the long chain dicarboxylic acid is at least one selected from C12 to C16 dicarboxylic acids or at least one selected from normal C12 to C16 dicarboxylic acids; and/or the modified long chain dicarboxylic acid-producing strain is able to produce the long chain dicarboxylic acid at pH 7.0 or lower, preferably 4.0 to 6.8, more preferably 5.0 to 6.5, compared to the strain before modified.

In some embodiments, the method comprises the steps of:
1) preparing a fragment of a target gene having a mutation by error-prone PCR;
2) preparing upstream and downstream fragments of the target gene necessary for homologous recombination as template for homologous recombination and a resistance marker gene, preferably the resistance marker gene is a hygromycin B resistance gene;
3) preparing a complete recombinant fragment by PCR overlap extension;
4) introducing the recombinant fragment into a strain using homologous recombination;
5) screening out a positive strain using the resistance marker;
6) screening out a strain with an increased long chain dicarboxylic acid yield and/or with the ability to produce a long chain dicarboxylic acid at an acidic pH;
7) optionally, the screened strain is further subjected to homologous recombination to remove the resistance marker.

In other words, the starting strain of the invention is the strain *Candida tropicalis* CATN145 (Deposit No. CCTCC M 2011192, deposited at China Center for Type Culture Collection on Jun. 9, 2011), which is a basic producing strain, and in the acid-producing period of the preparation of dicarboxylic acid by fermentation, during the fermentation process, in particular during the conversion period of the fermentation system, it is necessary to add an alkali liquor to the fermentation medium to maintain an alkaline culture condition to produce the dicarboxylic acid. In the invention, the CYP52A12 gene was randomly mutated by error-prone PCR, and the gene is subjected to directed evolution through homologous recombination to screen out a strain capable of producing a long chain dicarboxylic acid under an acidic condition.

Through the screening, a strain capable of producing a long chain dicarboxylic acid under an acidic culture condition is obtained in the invention, and its fermentation cycle is significantly shortened. The strain is designated as mutant strain 540. According to sequencing analysis, it is found that compared to the parent strain CCTCC M 2011192, the following base mutations occurred in the CYP52A12 gene of the mutant strain 540, taking the first base of the start codon ATG as 1: c.226A>G, c.960C>A, and c.1408G>A.

Preferably, according to the invention, the sequence of the CYP52A12 gene of the *Candida tropicalis* mutant strain is set forth in SEQ ID NO: 10 or 11.

By directed evolution of CYP52A12 gene, the invention screened out one strain which has a base mutation at the promoter region of said gene and is capable of producing a long chain dicarboxylic acid under an acidic condition. The establishment of an acidic culture condition does not require addition of a large amount of alkali during the acid producing process to maintain an alkaline environment, which simplifies the subsequent extraction process of the dicarboxylic acid product, and avoids the production of a large amount of high-salt wastewater during the fermentation process, greatly reducing adverse effects on the environment. In addition, the strain produces the acid in high concentration and shortens the fermentation cycle significantly. Compared to the prior production process, it not only has significant cost advantages, but also can effectively reduce the pressure on resources and environment. Therefore, it has very remarkable industrialization advantages.

In the fifth aspect, the invention relates to an isolated modified CYP52A12 protein, wherein, with reference to the amino acid numbering of SEQ ID NO: 20, the modified CYP52A12 protein comprises Asp at a position corresponding to the position 76 of SEQ ID NO: 20 and Ile at a position corresponding to the position 470 of SEQ ID NO: 20, compared to an unmodified CYP52A12 protein.

In an embodiment, the unmodified CYP52A12 protein comprises the amino acid sequence set forth in SEQ ID NO: 20.

In an embodiment, the modified CYP52A12 protein comprises an amino acid sequence having at least or at least about 70%, such as at least or at least about 75%, 80%, 85%, 90%, 91%, 92%, 93%, 94%, 95%, 96%, 97%, 98%, 99%, 99.2%, 99.4%, 99.6% or more sequence identity with SEQ ID NO: 20, and comprises a replacement of Asn with Asp at a position corresponding to the position 76 of SEQ ID NO: 20 and a replacement of Val with Ile at a position corresponding to the position 470 of SEQ ID NO: 20.

In an embodiment, the modified CYP52A12 protein comprises the amino acid sequence set forth in SEQ ID NO: 21.

In the sixth aspect, the invention relates to an isolated nucleic acid molecule comprising a nucleotide sequence encoding the modified CYP52A12 protein according to the invention.

In the seventh aspect, the invention relates to a vector comprising a nucleic acid molecule comprising a nucleotide sequence encoding the modified CYP52A12 protein according to the invention. In embodiments, the vector is a prokaryotic vector, a virus vector or a eukaryotic vector, such as the vector pCIB2 of SEQ ID NO: 3.

In the eighth aspect, the invention relates to a microorganism containing a modified CYP52A12 protein according to the invention, a nucleic acid molecule comprising a nucleotide sequence encoding the modified CYP52A12 protein according to the invention, and/or a vector comprising a nucleic acid molecule comprising a nucleotide sequence encoding the modified CYP52A12 protein according to the invention.

In an embodiment, said microorganism is selected from the group consisting of *Corynebacterium, Geotrichum candidum, Candida, Pichia, Rhodotroula, Saccharomyces* and *Yarrowia*, more preferably said microorganism is yeast, and more preferably said microorganism is *Candida tropicalis* or *Candida sake*.

A strain capable of producing a long chain dicarboxylic acid under an acidic culture condition is obtained in the invention, and its fermentation cycle is significantly shortened. The strain is designated as mutant strain 540. According to sequencing analysis, it is found that compared to the parent strain CCTCC M 2011192, the strain 540 contains a modified CYP52A12 protein according to the invention, wherein, with reference to the amino acid numbering of SEQ ID NO: 20, the modified CYP52A12 protein comprises Asp at a position corresponding to the position 76 of SEQ ID NO: 20 and Ile at a position corresponding to the position 470 of SEQ ID NO: 20.

Preferably, the modified CYP52A12 protein contained in the mutant *Candida* strain according to the invention comprises the amino acid sequence set forth in SEQ ID NO: 21.

In the ninth aspect, the invention relates to a method for producing a long chain dicarboxylic acid using the modified microorganism according to the eighth aspect, comprising a step of culturing the modified microorganism, preferably producing the long chain dicarboxylic acid under an acidic culture condition, optionally further comprising the step of isolating and purifying the long chain dicarboxylic acid from cultured products.

In an embodiment, the long chain dicarboxylic acid is selected from the group consisting of C9-C22 long chain dicarboxylic acids, preferably C9-C18 long chain dicarboxylic acids, more preferably selected from one or more of the group consisting of sebacic acid, undecanedioic acid, dodecanedioic acid, tridecanedioic acid, tetradecanedioic acid, pentadecanedioic acid and hexadecanedioic acid, and more preferably the long chain dicarboxylic acid is at least one selected from C12 to C16 dicarboxylic acids or at least one selected from normal C12 to C16 dicarboxylic acids; and/or the modified long chain dicarboxylic acid producing strain is able to produce the long chain dicarboxylic acid at pH 7.0 or below, preferably 4.0 to 6.8, and more preferably pH 5.0 to 6.5, compared to the strain before modified.

In the tenth aspect, the invention relates to a method of modifying a long chain dicarboxylic acid producing strain by directed evolution of the CYP52A12 gene, wherein the modified long chain dicarboxylic acid producing strain is capable of producing the long chain dicarboxylic acid under an acidic culture condition compared to the strain before modified, and wherein the modified long chain dicarboxylic acid producing strain comprises a mutant CYP52A12 gene encoding a modified CYP52A12 protein, wherein, with reference to the amino acid numbering of SEQ ID NO: 20, the modified CYP52A12 protein comprises Asp at a position corresponding to the position 76 of SEQ ID NO: 20 and Ile at a position corresponding to the position 470 of SEQ ID NO: 20, compared to an unmodified CYP52A12 protein.

In an embodiment, the unmodified CYP52A12 protein comprises the amino acid sequence set forth in SEQ ID NO: 20.

In an embodiment, the modified CYP52A12 protein comprises an amino acid sequence having at least or at least about 70%, such as at least or at least about 75%, 80%, 85%, 90%, 91%, 92%, 93%, 94%, 95%, 96%, 97%, 98%, 99%, 99.2%, 99.4%, 99.6% or more sequence identity with SEQ ID NO: 20, and comprises replacements of Asn with Asp at a position corresponding to the position 76 of SEQ ID NO: 20 and of Val with Ile at a position corresponding to the position 470 of SEQ ID NO: 20.

In an embodiment, the modified CYP52A12 protein comprises the amino acid sequence set forth in SEQ ID NO: 21.

BRIEF DESCRIPTION OF THE FIGURES

FIG. 2 is the alignment of the nucleotide sequences of the CYP52A12 gene in the mutant strain (SEQ ID NO:11) of the invention and the original strain (SEQ ID NO:22) and the mutation site is indicated with a black box.

DETAILED DESCRIPTION

Definition

Figure 1:
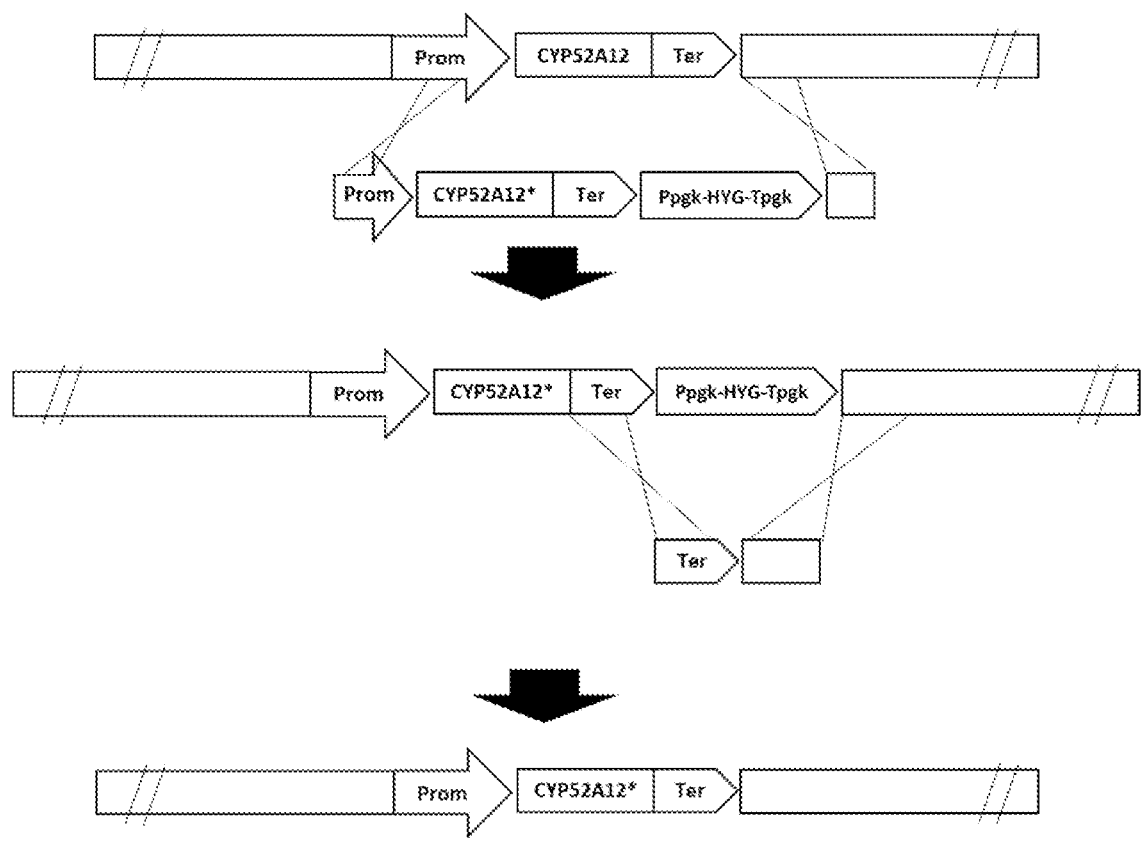
FIG. 1 is a schematic representation of the integration of the gene CYP52A12 with mutation sites and the removal of the hygromycin selection marker by homologous recombination. "*" indicates the mutation that may be present in any region of CYP52A12 (including the promoter, coding region and terminator).

Unless defined otherwise, technical and scientific terms used herein have the same meanings as commonly understood by skilled persons in the art. See e.g. Singleton et al., DICTIONARY OF MICROBIOLOGY AND MOLECULAR BIOLOGY $2^{nd}$ ed., J. Wiley & Sons (New York, N.Y. 1994); Sambrook et al., MOLECULAR CLONING, A LABORATORY MANUAL, Cold Springs Harbor Press (Cold Springs Harbor, 1989).

Long chain alkane: the substrate for fermentation of the invention includes a long chain alkane, which belongs to a saturated aliphatic hydrocarbon, a saturated hydrocarbon among hydrocarbons; its whole structure is mostly composed only of carbon, hydrogen, carbon-carbon single bond, and carbon-hydrogen single bond. It includes an alkane of the formula $CH_3(CH_2)nCH_3$, $n \geq 7$. Preferred are C9-C22 normal alkanes, more preferred are C9-C18 normal alkanes, and most preferred C10, C11, C12, C13, C14, C15, or C16 normal alkanes.

Long chain dicarboxylic acid (LCDA; also known as long chain diacid, hereinafter abbreviated as dicarboxylic acid) includes a diacid of the formula $HOOC(CH_2)nCOOH$, $n \geq 7$. Preferably, the long chain dicarboxylic acid comprises C9-C22 long chain dicarboxylic acids, preferably C9-C18 long chain dicarboxylic acids, more preferably one or more of sebacic acid, undecanedioic acid, dodecanedioic acid, tridecanedioic acid, tetradecanedioic acid, pentadecanedioic acid and hexadecanedioic acid. Preferably the long chain dicarboxylic acid is at least one of C12 to C16 dicarboxylic acids, and preferably at least one of normal C12 to C16 dicarboxylic acids.

Long chain dicarboxylic acid producing microorganism: a strain that has been reported to produce and accumulate a dicarboxylic acid includes a bacterium, yeast and mold, such as *Corynebacterium, Geotrichum candidum, Candida, Pichia, Rhodotroula, Saccharomyces, Yarrowia* and the like. Among them, many species of *Candida* are good strains for fermentative production of a dicarboxylic acid. The strain for fermentation preferably includes: *Candida tropicalis* or *Candida sake*.

CYP52A12 refers to one of the cytochrome oxidase P450 family CYP52 subfamily, which involves in the ω-oxidation of alkanes and lipids during the acid production of fermentation. One skilled in the art knows that CYP52A12 or its homologous gene is also present in other long chain dicarboxylic acid producing microorganisms, which sequences may be different, but play the same functions, and thus also fall within the scope of the invention.

The terms "polypeptide", "peptide" and "protein" are used interchangeably herein to refer to a polymer of amino acid residues, wherein optionally the polymer may be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers.

Unless indicated otherwise, the abbreviations for any nucleotides, amino acids and other compounds used herein are commonly used and recognized abbreviations or according to the IUPAC-IUB Commission on Biochemical Nomenclature ((1972) Biochem. 11:1726). Abbreviations for amino acid residues are shown in Table 1:

TABLE 1

| Symbol | | |
|---|---|---|
| 1-Letter | 3-Letter | Amino acid |
| Y | Tyr | Tyrosine |
| G | Gly | Glycine |
| F | Phe | Phenylalanine |
| M | Met | Methionine |
| A | Ala | Alanine |
| S | Ser | Serine |
| I | Ile | Isoleucine |
| L | Leu | Leucine |
| T | Thr | Threonine |
| V | Val | Valine |
| P | Pro | Proline |
| K | Lys | Lysine |
| H | His | Histidine |
| Q | Gln | Glutamine |
| E | Glu | Glutamic acid |
| W | Trp | Tryptophan |
| R | Arg | Arginine |
| D | Asp | Aspartic acid |
| N | Asn | Asparagine |
| C | Cys | Cysteine |

It should be noted that the amino acid sequences herein have a left to right orientation in the conventional direction of amino-terminus to carboxyl-terminus. It is known in the art that one amino acid may be encoded by one or more corresponding codons, and in various organisms, one can select suitable codon(s) for a desired amino acid, which fall within the scope of skill of one of ordinary skill in the art.

The term "isolated", when applied to a nucleic acid or protein, means that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

As used herein, the base mutation "c.XXX N0>N1" means that the base N0 at position XXX of the coding region is mutated to the base N1. For example, the base mutation c.226A>G means that, taking the first base "A" of the starting codon ATG of the coding region as 1, the base "A" at position 226 of the coding region is mutated to "G". In an embodiment, the sequence of the coding region of the gene CYP52A12 according to the invention is set forth in the nucleotides 1177 to 2748 of SEQ ID NO: 19. Herein, where a base is mentioned, G refers to guanine, T refers to thymine, A refers to adenine, C refers to cytosine, and U refers to uracil.

As used herein, "unmodified CYP52A12 protein" refers to a starting protein that is selected for modification according to the invention. The starting polypeptide can be a naturally-occurring, wild-type form of a protein, e.g. the CYP52A12 protein in the GenBank with accession number of AAO73952.1. Exemplary of an unmodified CYP52A12 protein is set forth in SEQ ID NO: 20. In addition, the starting polypeptide can be altered or mutated, such that it differs from a native wild type isoform but is nonetheless referred to herein as a starting unmodified protein relative to the subsequently modified protein produced herein. Thus, existing proteins known in the art that have been modified to have a desired increase or decrease in a particular activity or property compared to an unmodified reference protein can be selected and used as the starting unmodified protein. In an embodiment, the invention provides an isolated modified CYP52A12 protein, which comprises Asp at a position corresponding to the position 76 of SEQ ID NO: 20 and Ile at a position corresponding to the position 470 of SEQ ID NO: 20, compared to an unmodified CYP52A12 protein.

The terms "with reference to" or "corresponding to" when used in the context of the numbering of a given amino acid or polynucleotide sequence, refers to the numbering of the residues of a reference sequence when the given amino acid or polynucleotide sequence is compared to the reference sequence. An amino acid residue in a protein or a base in a nucleic acid "corresponds" to a given residue or base when it occupies the same essential structural position within the protein or nucleic acid as the given residue or base. For example, in some embodiments, where a selected protein is aligned for maximum homology with the reference sequence, an amino acid residue in the selected protein occupies the same structural position with the amino acid residue at position 67 of the reference sequence, the position of the aligned amino acid residue in the selected protein is said to correspond to position 67 of the reference sequence. Instead of a primary sequence alignment, a three dimensional structural alignment can also be used, e.g., where the structure of the selected protein is aligned for maximum correspondence with the reference sequence, and the overall structures are compared.

In general, to identify corresponding positions, the sequences of amino acids are aligned so that the highest order match is obtained (see, e.g. Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; Carillo et al. (1988) SIAM J Applied Math 48: 1073). Alignment of amino acid sequences, and to some extent nucleotide sequences, also can take into account conservative differences and/or frequent substitutions in amino acids (or nucleotides). Conservative differences are those that preserve the physico-chemical properties of the residues involved. Alignments can be global (alignment of the compared sequences over the entire length of the sequences and including all residues) or local (alignment of a portion of the sequences that includes only the most similar region(s)).

As used herein, the terms "homology" and "identity" are used interchangeably herein to refer to the extent of non-variance of amino acid or nucleotide sequences, which can be detected through the number of identical amino acids (or nucleotide bases) by aligning a polypeptide (or polynucleotide) with a reference polypeptide (or polynucleotide), and the protein homology may include conservative amino acid alteration. The sequence identity can be determined by standard alignment algorithm programs used with default gap penalties established by each supplier. Homologous polypeptides refer to a pre-determined number of identical or homologous amino acid residues. Homology includes conservative amino acid substitutions as well as identical residues. Homologous nucleic acid molecules refer to a pre-determined number of identical or homologous nucleotides. Homology includes substitutions that do not change the encoded amino acid ("silent substitution") as well as identical residues. Substantially homologous nucleic acid molecules hybridize typically at moderate stringency or high stringency all along the length of the nucleic acid or along at least about 70%, 80% or 90% of the full-length nucleic acid molecule of interest. Nucleic acid molecules that contain degenerate codons in place of codons in the hybridizing nucleic acid molecule are also contemplated in the invention. Whether any two nucleic acid molecules have nucleotide sequences (or any two polypeptides have amino acid sequences) that are at least 80%, 85%, 90%, 95%, 96%, 97%, 98% or 99% "identical" can be determined using a known computer algorithm such as the BLASTP, BLASTN, FASTA, DNAStar and Gap (University of Wisconsin Genetics Computer Group (UWG), Madison Wis., USA). Percent homology or identity of proteins and/or nucleic acid molecules can be determined, e.g. by comparing sequence information using a GAP computer program (e.g., Needleman et al. J. Mol. Biol. 48: 443 (1970), as revised by Smith and Waterman (Adv. Appl. Math. 2: 482 (1981)). Briefly, a GAP program defines similarity as the number of aligned symbols (i.e., nucleotides or amino acids) which are similar, divided by the total number of symbols in the shorter of the two sequences.

The modified CYP52A12 protein according to the invention may comprise e.g. 1, 2, 3, 4, 5, 6, 7, 8, 9, 10, 15, 20, 30, 40, 50 or more, additional amino acid modifications at other positions, such as insertion, deletion or replacement, in addition to the replacements at positions corresponding to positions 76 and 470 of SEQ ID NO: 20, provided that said additional modification(s) do not substantially reduce the activity of the modified CYP52A12 protein for producing a long chain dicarboxylic acid under an acidic culture condition. The expression "not substantially reduce" refers to that under the same conditions (e.g. acidic culture condition), the acid production (e.g. in unit of mg of dicarboxylic acid per g of fermentation broth) of a microorganism comprising a modified CYP52A12 protein comprising said additional modification(s) is reduced by no more than 50%, 40%, 30%, 20%, 10%, 5%, 4%, 3%, 2%, 1% or less, compared to a microorganism comprising the modified CYP52A12 protein comprising the amino acid sequence of SEQ ID NO: 21.

In an embodiment, the modified CYP52A12 protein according to the invention comprises an amino acid sequence having at least or at least about 70%, such as at least or at least about 75%, 80%, 85%, 90%, 91%, 92%, 93%, 94%, 95%, 96%, 97%, 98%, 99%, 99.2%, 99.4%, 99.6% or more sequence identity with SEQ ID NO: 20, and comprises a replacement of Asn with Asp at a position corresponding to the position 76 of SEQ ID NO: 20 and a replacement of Val with Ile at a position corresponding to the position 470 of SEQ ID NO: 20.

In an embodiment, the modified CYP52A12 protein according to the invention possesses the activity of the cytochrome oxidase P450 family CYP52 subfamily, e.g., the activity of ω-oxidizing alkanes and lipids during acid production by fermentation. In an embodiment, the modified CYP52A12 protein according to the invention possesses the capability of producing a long chain dicarboxylic acid under an acidic culture condition, e.g. under the same conditions, the capability of the modified CYP52A12 protein (e.g. acid production, e.g. in unit of mg of dicarboxylic acid per g of fermentation broth) is at least or at least about 50%, 60%, 70%, 80%, 90%, 95%, 96%, 97%, 98%, 99% or more of that of the modified CYP52A12 protein comprising the amino acid sequence set forth in SEQ ID NO: 21.

In an embodiment, the modified CYP52A12 protein according to the invention is derived from *Candida*, *Pichia*, *Rhodotroula*, *Saccharomyces* or *Yarrowia*, more preferably *Candida tropicalis* or *Candida sake*.

Homologous gene refers to two or more gene sequences whose sequence similarity is up to 80%, including an orthologous gene, a paralogous gene and/or a xenologous gene. The homologous gene of the CYP52A12 gene in the invention refers to either an orthologous gene of the CYP52A12 gene, or a paralogous gene or a xenologous gene of the CYP52A12 gene.

Sequence identity refers to the percentage of the identical bases between the residues of a polynucleotide sequence variant and the bases of the non-variant sequence after sequence alignment and/or introduction of gaps. In some embodiments, the polynucleotide variants have at least or at least about 70%, 75%, 80%, 90%, 95%, 96%, 97%, 98%, 99%, 99.1%, 99.2%, 99.3%, 99.4%, 99.5%, 99.6%, 99.7%, 99.8%, 99.9%, 99.91%, 99.92%, 99.93%, 99.94%, 99.95%, or 99.96% polynucleotide homology to the polynucleotide described herein.

Directed evolution refers to the process of simulating natural selection by technology means. Through artificially created mutations and specific selection pressure, a protein or nucleic acid is mutated into a specific direction; thereby achieving an evolution process in a short period of time at molecule level that needs thousands of years to be completed in nature.

In some embodiments, in the error-prone PCR of the disclosure, the concentration of $Mg^{2+}$ is in a range from 1 to 10 mM, preferably 2 to 8 mM, more preferably 5 to 6 mM, and/or the concentration of dNTP is 0.1 to 5 mM, preferably 0.2 to 3 mM, more preferably 0.5 to 2 mM, and more preferably 0.8 to 1.5 mM, for example 1 mM, and/or addition of freshly prepared $MnCl_2$ to a final concentration of 0.1 to 5 mM, preferably 0.2 to 2 mM, more preferably 0.3 to 1 mM, and more preferably 0.4 to 0.7 mM, for example 0.5 mM. In some embodiments, the probability of mutation is increased by decreasing the amount of template and appropriately increasing PCR cycles to 40 or more, e.g. 41, 42, 43, 44, 45, 46, 47, 48, 49, 50, 55, 60 or more cycles.

PCR overlap extension, also known as SOE (gene splicing by overlap extension) PCR, refers to a method of splicing different DNA fragments together via PCR amplification by designing primers having complementary ends.

Homologous recombination refers to a recombination between DNA molecules that relies on sequence similarity, most commonly found within a cell to repair a mutation that occurs during mitosis. Homologous recombination technology has been widely used in genome editing, including gene knockout, gene repair, and introduction of a new gene to a specific site. A class of microorganisms represented by *Saccharomyces cerevisiae* has a very high probability of homologous recombination occurring in their cells, independent on sequence specificity, and has obvious advantages in genome editing. Site-specific recombination relies on the participation of a specific site and a site-specific recombinase, and the recombination occurs only between specific sites, such as Cre/loxP, FLP/FRT and the like. The homologous recombination technology used in the disclosure does not belong to site-specific recombination, and the recombination relies on an intracellular DNA repair system.

The resistance marker is one of selection markers that often carry the ability to confer the transformant survival in the presence of an antibiotic. The resistance marker gene includes NPT, HPT, BLA, HYG and CAT, etc., which are resistant to kanamycin, hygromycin, ampicillin/carbenicillin, and chloramphenicol, respectively. Preferably, the resistance marker gene is the hygromycin B resistance gene HYG.

The alkaline culture condition refers to that the pH of the fermentation system is controlled to be maintained at a range greater than 7.0 during the acid production of the fermentation substrate, e.g. 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.2, 9.4, 9.6 or higher. The controlled pH of the fermentation system is preferably the pH during the conversion period of the fermentation system, i.e., when cell optical density ($OD_{620}$) greater than 0.5 (30-fold dilution).

The acidic culture condition refers to that the pH of the fermentation system is controlled to be maintained at a range less than 7.0 during the acid production of the fermentation substrate. Preferably, the acidic culture condition refers to that the pH of the fermentation system is controlled to be maintained at a range of pH 4.0 to pH 6.8. More preferably, the acidic culture condition refers to the pH in a range of pH 5.0 to pH 6.5. Preferably, the controlled pH of the fermentation system is the pH during the conversion period of the fermentation system, i.e., when cell optical density ($OD_{620}$) is greater than 0.5 (30-fold dilution), the pH of the fermentation system is controlled to be below 7.0, preferably 4.0 to 6.8, more preferably 5.0 to 6.5. Particularly, the pH of the fermentation system is controlled to be: 3, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, or 7.0.

The ways for adjusting or controlling the pH value is not particularly limited in the disclosure, and it may be controlling a constant pH value, not controlling pH value, a pH value not lower than a certain value, a pH value not more than a certain value, up-regulating pH value, down-regulating pH value, controlling or naturally letting pH value to fall within a certain range from outside the range, or a combination of any of these ways. The method for regulating the pH value is not limited in the disclosure, and a conventional method in the art of fermentation can be used, for example, adding an alkaline solution at a proper concentration.

During fermentation, the fermentation medium includes a carbon source, a nitrogen source, an inorganic salt and a nutritional factor.

In some embodiments, the carbon source comprises one or more selected from the group consisting of glucose, sucrose and maltose; and/or the carbon source is added in an amount of 1% to 10% (w/v), such as 1.5%, 2.0%, 2.5%, 3.0%, 3.5%, 4.0%, 4.5%, 5.0%, 6.0%, 7.0%, 8.0%, or 9.0%.

In some embodiments, the nitrogen source comprises one or more selected from the group consisting of peptone, yeast extract, corn syrup, ammonium sulfate, urea and potassium nitrate; and/or the nitrogen source is added in a total amount of 0.1% to 3% (w/v), such as 0.2%, 0.4%, 0.5%, 0.6%, 0.8%, 1.0%, 1.2%, 1.5%, 1.8%, 2.0%, or 2.5%.

In some embodiments, the inorganic salt comprises one or more selected from the group consisting of potassium dihydrogen phosphate, potassium chloride, magnesium sulfate, calcium chloride, iron chloride and copper sulfate; and/or the inorganic salt is added in a total amount of 0.1% to 1.5% (w/v), such as 0.2%, 0.3%, 0.4%, 0.5%, 0.6%, 0.7%, 0.8%, 0.9%, 1.0%, 1.1%, 1.2%, 1.3%, or 1.4%.

In some embodiments, the nutritional factor comprises one or more selected from the group consisting of vitamin B1, vitamin B2, vitamin C, and biotin; and/or the nutritional factor is added in a total amount of 0 to 1% (w/v), such as 0.2%, 0.3%, 0.4%, 0.5%, 0.6%, 0.7%, 0.8%, or 0.9%. According to common knowledge in the field of fermentation, the percentage in the disclosure is the mass to volume ratio, i.e., w/v; % indicates g/100 mL.

Those skilled in the art can easily determine the amount of the above substances added.

In one embodiment of the disclosure, the inoculation amount of the fermentation strain is 10% to 30%, for example, 11%, 12%, 13%, 14%, 15%, 16%, 17%, 18%, 19%, 20%, 22%, 24%, 25%, 27%, or 29%. When the strain is cultured to an optical density ($OD_{620}$) of 0.5 or more (diluted 30 folds), the substrate is added for fermentation conversion.

As used herein, "optional" or "optionally" means that the subsequently described event or circumstance does or does not occur, and that the description comprises instances where the event or circumstance occurs or does not occur. For example, "optionally a step" means that the step is present or not present.

As used herein, the term "about" means a range of values including the specified value, which a person of ordinary skill in the art would consider reasonably similar to the specified value. In some embodiments, the term "about" means within a standard deviation using measurements generally acceptable in the art. In some embodiments, "about" means a range extending to +/−10% of the specified value.

The disclosure will be further illustrated by the following non-limiting examples. Those skilled in the art will recognize that many modifications can be made to the disclosure without departing from the spirit of the disclosure, and such modifications also fall within the scope of the disclosure.

The following experimental methods are all conventional methods unless otherwise specified, and the experimental materials used can be easily obtained commercially unless otherwise specified.

Example 1: Culture Media and Methods for Culture and Fermentation as Well as for Detecting a Dicarboxylic Acid 1. YPD medium formula (w/v) was: 2% peptone, 2% glucose and 1% yeast extract (OXOID, LP0021). 1.5-2% agar powder was added to form a solid media.

During culturing, a single colony was picked in a 2 ml centrifuge tube containing 1 ml YPD liquid medium, incubated at 30° C. in a 250 RPM shaker for 1 day.

2. Seed medium formula (w/v): sucrose 10 to 20 g/L, yeast extract 3 to 8 g/L, industrial fermentation corn syrup (for short, corn syrup, with total nitrogen content 2.5 wt %) 2 to 4 g/L, $KH_2PO_4$ 4 to 12 g/L, urea 0.5 to 4 g/L (separately sterilized at 115° C. for 20 min), and the substrate for fermentation was n-dodecane 20 mL/L.

During culturing, the inoculum obtained in step 1 was inoculated into a 500 mL shake flask containing 30 mL seed medium, wherein the amount of inoculum was 3-5%, and incubated at 30° C. in a 250 RPM shaker until $OD_{620}$ reached 0.8 (after 30-fold dilution).

3. Fermentation medium (w/v) comprises: sucrose 10-40 g/L, corn syrup (total nitrogen content 2.5 wt %) 1 to 5 g/L, yeast extract 4 to 12 g/L, NaCl 0 to 3 g/L, $KNO_3$ 4 to 12 g/L, $KH_2PO_4$ 4 to 12 g/L, urea 0.5 to 3 g/L (separately sterilized at 115° C. for 20 min), and the substrate for fermentation was n-dodecane 300 to 400 mL/L (as shown below), adjusting the pH to 4.5 to 7.5 using 1N HCl and 1N NaOH (as shown below).

During fermentation, the seed culture obtained in step 2 was inoculated into a 500 mL shake flask containing 15 mL fermentation medium, wherein the amount of inoculum was 10 to 30%, and the culture was incubated at 30° C. on a 250 RPM shaker for 90-144 h. During the culture, the pH was adjusted to the setting range by adding acid/alkali at a certain interval.

4. Determination of the long chain dicarboxylic acid yield by acid-base titration The pH of the fermentation broth was adjusted to 3.0 using 1N hydrochloric acid solution, and then 100 mL of ether was added to extract the long chain dicarboxylic acid in the fermentation broth, and then evaporated to remove ether to obtain a long chain dicarboxylic acid powder; the resulting long chain dicarboxylic acid powder was dissolved in ethanol, and titrated with NaOH solution at 0.1 mol/L to obtain the final dicarboxylic acid titer in the fermentation broth, and the long chain dicarboxylic acid yield was calculated accordingly.

Example 2: Preparation of CYP52A12 Mutation Template

1. Preparation of the CYP52A12 mutation template.

The genomic DNA of *Candida* CCTCC M 2011192 was extracted by using Ezup Yeast Genomic DNA Extraction Kit (Sangon, Cat No. 518257). A method with liquid nitrogen grinding was used in favor of increasing the cell wall disruption efficiency. Genomic DNA obtained by this method was used as template for error-prone PCR.

2. Error-prone PCR

The concentration of $Mg^{2+}$ was adjusted (2-8 mM) and the CYP52A12 gene was amplified by error-prone PCR using Taq DNA Polymerase (Takara, Cat No. R001B).

(PCR condition was: Step 1: 98° C. for 30 s, step 2: 98° C. for 10 s, 55° C. for 30 s, 72° C. for 2 m 20 s, 35 cycles in total, Step 3: 72° C. for 5 m).

The primers were as follows:

```
CYP52A12-F:
                                   (SEQ ID NO: 1)
5'-CAAAACAGCACTCCGCTTGT-3',

CYP52A12-R:
                                   (SEQ ID NO: 2)
5'-GGATGACGTGTGTGGCTTGA-3',
```

The PCR product was subjected to electrophoresis on a 1% agarose gel and recovered and purified by using the Axygen Gel Recovery Kit (Axygen, AP-GX-250G).

Example 3: Preparation of Homologous Recombination Template

All DNA fragments in this example were obtained by amplification using PrimeSTAR® HS High Fidelity DNA polymerase (Takara, R040A). The DNA fragments were subjected to electrophoresis on a 1% agarose gel, followed by recovery and purification by using the Axygen Gel Recovery Kit.

(1) Amplification of the resistance selection marker (HYG, the hygromycin resistance gene). The amplification template was the vector pCIB2 (SEQ ID NO: 3) owned by our company. The primer sequences were as follows:

```
CYP52A12_HYG-F:
                                          (SEQ ID NO: 4)
5'-TCAAGCCACACACGTCATCCGCATGCGAACCCGAAAATGG-3',

CYP52A12_HYG-R:
                                          (SEQ ID NO: 5)
5'-GATGTGGTGATGGGTGGGCTGCTAGCAGCTGGATTTCACT-3'.
```

The PCR reaction condition was as follows:
Step 1: 98° C. for 30 s,
Step 2: 98° C. for 10 s, 55° C. for 30 s, 72° C. for 1 m 50 s, 5 cycles,
Step 3: 98° C. for 10 s, 72° C. for 2 m, 25 cycles,
Step 4: 72° C. for 5 m.

The resulting product, named HYG, was verified by sequencing, as shown in SEQ ID NO: 6.

(2) Amplification of the downstream fragment for homologous recombination. The template was the genomic DNA of the above *Candida tropicalis*. The primer sequences were as follows:

```
CYP52A12_Down-F:
                                          (SEQ ID NO: 7)
5'-AGCCCACCCATCACCACATC-3', CYP52A12_Down-R:
                                          (SEQ ID NO: 8)
5'-CGAAGTCGTAATCCGCAACG-3'.
```

The PCR reaction condition was as follows:
Step 1: 98° C. for 30 s,
Step 2: 98° C. for 10 s, 55° C. for 30 s, 72° C. for 1 m 40 s, 30 cycles,
Step 3: 72° C. for 5 m.

The resulting product, named CYP52A12_Down, was verified by sequencing, the sequence as shown in SEQ ID NO: 9.

(3) PCR overlap extension to obtain a complete recombination template.

The three PCR fragments recovered above were subjected to overlap extension to obtain a template for homologous recombination, which was recovered and purified. The specific method was as follows:

Overlap extension PCR was performed by adding an equimolar amount of CYP52A12, HYG and CYP52A12_Down fragments as templates, using primers CYP52A12_Down-F and CYP52A12_Down-R, and using PrimeSTAR® HS High Fidelity DNA polymerase. The recombination fragment with a size of approximately 4.3 Kb was recovered and purified after gel electrophoresis.

The PCR reaction condition was as follows:
Step 1: 98° C. for 30 s,
Step 2: 98° C. for 10 s, 55° C. for 30 s, 72° C. for 4 m 30 s, 30 cycles,
Step 3: 72° C. for 5 m.

The recombination fragment of approximately 4.3 Kb was recovered and purified after gel electrophoresis, and verified by sequencing, whose sequence was shown in SEQ ID NO: 10.

FIG. 1 is a schematic representation of the integration of the CYP52A12 gene having mutation sites and the removal of the hygromycin selection marker by homologous recombination.

Example 4: Construction of *Candida tropicalis* CYP52A12 Gene Mutant Library

1. Preparation of Yeast Electroporation-competent Cells

The yeast cells CCTCC M 2011192 subjected to overnight incubation at 30° C. on a 250 rpm shaking were inoculated into 100 mL YPD medium to $OD_{620}$ of 0.1. Under the same conditions, the cells were cultured to $OD_{620}$ of 1.3. The cells were collected by centrifugation at 3000 g, 4° C. The cells were washed twice with ice-cold sterile water and collected, and then resuspended in 10 ml of ice-cold 1M sorbitol solution. The cells were collected by centrifugation at 4° C., 1500 g and resuspended in 1 ml of sorbitol solution as above. 100 μL aliquot of cell suspension was made for genetic transformation.

2. Competent Yeast Cell Electroporation

1 μg of the DNA fragment used for genetic transformation recovered in step (3) of Example 3 was added to the above competent cells. The cells were placed on ice for 5 min and quickly transferred to a 0.2 cm cuvette, and after electroporation (BioRad, Micropulser™ Electroporator, program SC2), 1 mL of a mixture of YPD and 1M sorbitol (1:1, v/v) was immediately added, and incubated at 30° C. at 200 rpm for 2 hours. The cells were collected and plated on a YPD medium plate with 100 mg/L of hygromycin B, and cultured at 30° C. for 2-3 days until single colonies appeared.

Example 5: Screening of Mutant Strains

1. Screening method: single colonies obtained in Example 4 were picked into a 2 ml centrifuge tube with 1 ml of YPD medium of Example 1 (containing hygromycin B at 100 mg/L), incubated at 30° C. in a 250 RPM shaker for 1 day. The above solution was inoculated into a 500-mL shake flask with 30 ml of the seed medium of Example 1 (containing hygromycin B at 100 mg/L). The inoculum amount was 3%, cultured at 250 rpm and 30° C. until $OD_{620}$ reached 0.8 (after 30-fold dilution). The seed liquid was inoculated into a 500-mL shake flask containing 15 ml of the fermentation medium of Example 1, wherein the inoculum amount was 20%, and the pH was adjusted to 5.5 every one hour, and the substrate was n-dodecane in the fermentation medium. The culture at 250 rpm and 30° C. was continued until the end of the fermentation, and the fermentation time was counted. The strain CCTCC M 2011192 was used as control: the culture medium, incubation and fermentation methods were the same as above except that the pH of the fermentation system was controlled to be 7.5 during the fermentation.

A 0.5 g sample of the fermentation broth was taken and subjected to acid-base titration using the method described in Example 1.4., and the yield of the dicarboxylic acid was calculated accordingly.

2. Screening results: a strain capable of producing a dicarboxylic acid under an acidic culture condition was obtained after screening. Compared with the parent strain CCTCC M 2011192, the fermentation time was reduced by 25 hours. This strain was designated as 540HYG. The results were shown in Table 1.

TABLE 1

|  | CCTCC M 2011192 at pH 7.5 | 540HYG at pH 5.5 |
|---|---|---|
| Fermentation time (h) | 129 | 104 |
| Acid yield (mg/g) | 150.9 | 141.8 |

Example 6: Sequence Analysis of CYP52A12 Gene in Mutant Strain 540HYG

1. According to the method of Example 2, CCTCC M 2011192 and 540HYG genomic DNAs were extracted, and CYP52A12 gene region was amplified using PrimeSTAR® HS High Fidelity DNA polymerase (Takara), using the primers CYP52A12-F and CYP52A12-R. The PCR reaction condition was the same as above.

2. After completion of the PCR, the product was subjected to gel electrophoresis and recovered and purified.

3. Addition of A to the purified PCR fragment: 20 µL of the recovered PCR fragment was added to 4 µL of 10× Takara Taq Buffer, 3.2 µL of dNTPs (each 10 mM) and 0.2 µL of Takara Taq, supplemented with ddH$_2$O to a volume of 40 µL, mixed well and incubated at 72° C. for 20 minutes, and recovered by Axygen PCR purification kit.

4. TA cloning. 4 µL of the recovered PCR fragment after addition of A in step 3 was added to 1 µL pMD19-T vector backbone and 5 µL Solution I, mixed well and incubated at 16° C. for 30 min. The ligation product was transformed into DH5α chemical competent cells and positive clones were picked and sent to Majorbio for sequencing.

The results showed that: compared with the parent strain CCTCC M 2011192, several base mutations occurred in the coding region of the screened strain 540HYG, as shown in the black box in the sequence alignment of FIG. 2. Its sequence was shown in SEQ ID NO: 11.

Example 7: Removal of the Resistance Selection Marker

1. Preparation of the template for homologous recombination with removal of the resistance selection marker Taking the *Candida tropicalis* mutant strain 540HYG genomic DNA as template, the recombinant template fragment for removing the resistance selection marker was amplified by PCR using PrimeSTAR® HS high-fidelity DNA polymerase, and recovered after gel electrophoresis. The sequence obtained was shown in SEQ ID NO: 12. The primer sequences were as follows:

```
CYP52A12_Ter-F:
                               (SEQ ID NO: 13)
5'-GTGCAGGACACAAACTCCCT-3',

CYP52A12_Down-R:
                               (SEQ ID NO: 14)
5'-CGAAGTCGTAATCCGCAACG-3'.
```

The PCR reaction condition was as follows:
Step 1: 98° C. for 30 s,
Step 2: 98° C. for 10 s, 55° C. for 30 s, 72° C. for 30 s, 30 cycles,
Step 3: 72° C. for 5 m.

2. Removal of the Resistance Selection Marker

Freshly electro-competent cells of the strain 540HYG were prepared and 0.3 µg of the recombinant fragment in step 1 was added. After placed on ice for 5 min, the cells were quickly transferred to a pre-chilled 0.2 cm cuvette on ice and transformed by electroporation (the same with above, 1.5 kV, 25 uFD, 200 ohms). A mixture of 1 mL YPD and 1M sorbitol (1:1, v/v) was quickly added, and incubated at 30° C. and 200 rpm for 2 hours. The cells were collected and plated on an YPD medium plate without an antibiotic, cultured at 30° C. for 2-3 days until single colonies appeared.

3. Screening for strains with the resistance marker removed

Single colonies were picked individually and inoculated on YPD plates with and without hygromycin (100 mg/L). Single colonies that can grow on the medium without antibiotics but not on medium with the antibiotic were picked and inoculated to a 2 mL centrifuge tube containing 1 mL of YPD medium, overnight incubated at 4° C. and 250 rpm, and the removal of the resistance selection marker was identified by colony PCR in the next day. The primers used were:

a) CYP52A12_Ter-F & CYP52A12_Down-R, PCR reaction condition was the same as above;

```
b) HYG-F:
                               (SEQ ID NO: 15)
5'-CTCGGAGGGCGAAGAATCTC-3',

HYG-R:
                               (SEQ ID NO: 16)
5'-CAATGACCGCTGTTATGCGG-3.
```

The PCR reaction condition was as follows:
Step 1: 98° C. for 30 s,
Step 2: 98° C. for 10 s, 55° C. for 30 s, 72° C. for 35 s, 30 cycles,
Step 3: 72° C. for 5 m.

4. Screening Results

By colony PCR, one strain with the resistance marker removed was screened out, and confirmed by sequencing, the method was the same as Example 6. The mutations present in the coding region of CYP52A12 gene of said strain were the same as the strain 540HYG, and the hygromycin selection marker gene was removed. The strain was eventually designated as 540.

Example 8: Fermentation Production of a Long Chain Dicarboxylic Acid by the Strain 540

The strain 540 was inoculated to a 2 ml centrifuge tube containing 1 ml of YPD medium of Example 1, cultured at 30° C. on a 250 RPM shaker for 1 day. The above culture was inoculated into a 500-mL shake flask with 30 ml of the seed medium of Example 1 at an inoculum amount of 3%, cultured in a 250 rpm shaker at 30° C. for 26 to 48 hours until OD$_{620}$ reached 0.8 (after 30-fold dilution). The seed liquid was inoculated into a shake flask containing 15 ml of the fermentation medium of Example 1 at an inoculum amount of 20%, and the pH was adjusted to 4.5 every one hour, and the substrate was n-dodecane in the fermentation medium. The culture at 250 rpm and 30° C. was continued until the end of the fermentation, and the fermentation time was counted. The dicarboxylic acid yield was determined by the method described in Example 1.4.

Comparative Example 1: Fermentation Production of a Long Chain Dicarboxylic Acid by the Strain CTCCC (China Center for Type Culture Collection) M 2011192

The culture medium, the culture method and the fermentation method were identical to those in Example 8, except that the inoculated strain was the strain CCTCC M 2011192, and the pH of the fermentation system during the fermentation was controlled to be 7.5. The fermentation time was counted, and the dicarboxylic acid yield was determined by the method described in Example 1.4.

Comparative Example 2: Fermentation Production of a Long Chain Dicarboxylic Acid by the Strain CTCCC M 2011192

The culture medium, the culture method and the fermentation method were identical to those in Example 8, except that the inoculated strain was the strain CCTCC M 2011192, and the pH of the fermentation system during the conversion of the fermentation was controlled to be 6.0. The fermentation time was counted, and the dicarboxylic acid yield was determined by the method described in Example 1.4.

Example 9

The culture medium, the culture method and the fermentation method were identical to those in Example 8, except that the pH of the fermentation system during the conversion of the fermentation was controlled to be 5.0.

Example 10

The culture medium, the culture method and the fermentation method were identical to those in Example 8, except that the pH of the fermentation system during the conversion of the fermentation was controlled to be 5.5.

Example 11

The culture medium, the culture method and the fermentation method were identical to those in Example 8, except that the pH of the fermentation system during the conversion of the fermentation was controlled to be 6.0.

Example 12

The culture medium, the culture method and the fermentation method were identical to those in Example 8, except that the pH of the fermentation system during the conversion of the fermentation was controlled to be 6.5.

Example 13

The culture medium, the culture method and the fermentation method were identical to those in Example 8, except that the pH of the fermentation system during the conversion of the fermentation was controlled to be 7.0

Example 14

The culture medium, the culture method and the fermentation method were identical to those in Example 8, except that the pH of the fermentation system during the conversion of the fermentation was controlled to be 7.5.

The statistical data of the Comparative Examples 1-2 and the Examples 8-14 were shown in Table 2 below. It can be seen that under an acidic condition, i.e. the pH of the fermentation system was less than 7, the strain 540 can not only produce more dicarboxylic acid, but also the fermentation time was significantly reduced.

TABLE 2

| | Strain CTCCC M 2011192 at pH X (X =) | | Strain 540 at pH X (X =) | | | | | | |
| --- | --- | --- | --- | --- | --- | --- | --- | --- | --- |
| Strain and pH condition | 7.5 Comparative Example 1 | 6.0 Comparative Example 2 | 4.5 Example 8 | 5.0 Example 9 | 5.5 Example 10 | 6.0 Example 11 | 6.5 Example 12 | 7.0 Example 13 | 7.5 Example 14 |
| Fermentation time (h) | 131 | 115 | 96 | 101 | 104 | 106 | 109 | 113 | 119 |
| Acid yield (mg/g) | 151.2 | 124.4 | 102.1 | 122.8 | 142.5 | 154.1 | 137.5 | 118.6 | 99.4 |

It can be seen from Table 2 that the acid yield of the strain 540 under an acidic condition at pH X (X=5.5, 6.0, 6.5) was comparable to that by the strain CCTCC M 2011192 under an alkaline condition, and even more, and the acidic fermentation condition allows that in the acid production process, it is not necessary to add a large amount of alkali to maintain the alkaline environment, which simplifies the extraction process of the dicarboxylic acid product and avoids the production of a large amount of high-salt wastewater during the fermentation process, which greatly reduces adverse impacts on the environment and reduces the fermentation time effectively.

Example 15

To further validate the mutations, the yeast 540HYG genomic DNA was extracted and the DNA fragment containing the mutant CYP52A12 and HYG resistance gene was amplified by PCR using PrimeSTAR® HS High Fidelity DNA polymerase, using the primers set forth in SEQ ID NO: 17 and SEQ ID NO: 8.

```
CYP52A12-F:
                                    (SEQ ID NO: 17)
5'-ATGGCCACACAAGAAATCATCG-3'

CYP52A12_Down-R:
                                    (SEQ ID NO: 8)
5'-CGAAGTCGTAATCCGCAACG-3'
```

The PCR reaction condition was as follows:
Step 1: 98° C. for 30 s,
Step 2: 98° C. for 10 s, 55° C. for 30 s, 72° C. for 2 m 20 s, 30 cycles,
Step 3: 72° C. for 5 m.

The fragment with a size of approximately 4.0 Kb was recovered and purified after gel electrophoresis, confirmed by sequencing, whose sequence was shown in SEQ ID NO: 18.

The process of homologous recombination for introducing the above DNA fragment (SEQ ID NO: 18) into the strain CCTCC M 2011192 was the same as that of Example 4. The sequencing step of the gene P450 in single colonies obtained by the screening was the same as that of Example 6. Confirmed by sequencing, the picked single colonies contained the gene P450 having the mutations integrated, and the mutation sites were consistent with SEQ ID NO: 11. One of the strains was named as 541HYG.

The fermentation time was measured in the same manner as in Example 5. The results showed that, consistent with 540HYG, the fermentation time of 541HYG was significantly shortened compared to the parent strain at pH 5.5. The results were shown in Table 3.

TABLE 3

| Strain and pH condition | Strain CTCCC M 2011192 at pH 7.5 | Strain 540HYG at pH 5.5 | Strain 541HYG at pH 5.5 |
|---|---|---|---|
| Fermentation time (h) | 130 | 106 | 105 |
| Acid yield (mg/g) | 149.8 | 142.7 | 143.4 |

Example 16

The DNA fragment (SEQ ID NO: 18) of the Example 15 was introduced into *Candida tropicalis* (CCTCC M 203052) by homologous recombination, via the process as described in Example 4. The sequencing step of the gene CYP52A12 in the genomes of single colonies obtained by the screening and of the parent strain (CCTCC M 203052) was the same as that of Example 6. Confirmed by sequencing, the sequence of the gene CYP52A12 of the parent strain (CCTCC M 203052) was identical to the sequence in the Genbank (Accession No.: AY230498 (SEQ ID NO: 19)) and the screened single colonies contained the gene having the mutations, and the mutation sites were consistent with SEQ ID NO: 11. One of the strains was named as 542HYG.

The fermentation time was measured in the same manner as in Example 5. The results showed that, the fermentation time of 542HYG was significantly shortened compared to the parent strain (CCTCC M203052) at pH 5.5. The results were shown in Table 4.

TABLE 4

| Strain and pH condition | Strain CCTCC M203052 at pH 7.5 | Strain 542HYG at pH 5.5 |
|---|---|---|
| Fermentation time (h) | 138 | 114 |
| Acid yield (mg/g) | 140.7 | 131.9 |

The invention claimed is:

1. A product comprising an isolated modified CYP52A12 protein, wherein, with reference to the amino acid numbering of SEQ ID NO:20, the modified CYP52A12 protein comprises Asp at a position corresponding to the position 76 of SEQ ID NO: 20 and Ile at a position corresponding to the position 470 of SEQ ID NO: 20, compared to an unmodified CYP52A12 protein, and wherein the modified CYP52A12 protein comprises an amino acid sequence at least 99% identical to SEQ ID NO. 20 and has the capability of producing a long chain dicarboxylic acid under an acidic culture condition that is at least 95% or more of that of the modified CYP52A12 protein comprising the amino acid sequence set forth in SEQ ID NO.21.

2. The product of claim 1, wherein the modified CYP52A12 protein comprises the amino acid sequence set forth in SEQ ID NO:21.

* * * * *